(12) United States Patent
Tkaczyk et al.

(10) Patent No.: US 7,606,347 B2
(45) Date of Patent: Oct. 20, 2009

(54) PHOTON COUNTING X-RAY DETECTOR WITH OVERRANGE LOGIC CONTROL

(75) Inventors: John Eric Tkaczyk, Delanson, NY (US); Jonathan D. Short, Saratoga Springs, NY (US); James Wilson Rose, Guilderland, NY (US); Xiaoye Wu, Rexford, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 178 days.

(21) Appl. No.: 11/744,292

(22) Filed: May 4, 2007

(65) Prior Publication Data

US 2007/0206721 A1 Sep. 6, 2007

Related U.S. Application Data

(63) Continuation-in-part of application No. 10/939,787, filed on Sep. 13, 2004, now Pat. No. 7,260,174.

(51) Int. Cl.
*A61B 6/03* (2006.01)
(52) U.S. Cl. ........................ 378/19; 378/98.8
(58) Field of Classification Search .............. 378/19, 378/98.7, 98.8; 250/370.09
See application file for complete search history.

(56) References Cited

U.S. PATENT DOCUMENTS

| | | | |
|---|---|---|---|
| 4,891,757 A * | 1/1990 | Shroy et al. | 378/98.7 |
| 5,218,624 A | 6/1993 | LeMay | |
| 5,225,980 A | 7/1993 | Hsieh et al. | |
| 5,228,069 A | 7/1993 | Arenson et al. | |
| 5,262,871 A | 11/1993 | Wilder et al. | |
| 5,376,795 A | 12/1994 | Hasegawa et al. | |
| 5,400,378 A | 3/1995 | Toth | |
| 5,448,185 A * | 9/1995 | Kaptanoglu | 326/39 |
| 5,548,123 A | 8/1996 | Perez-Mendez et al. | |
| 5,789,737 A | 8/1998 | Street | |
| 5,841,830 A * | 11/1998 | Barni et al. | 378/15 |
| 6,044,128 A * | 3/2000 | Tanaka et al. | 378/98.8 |
| 6,198,790 B1 | 3/2001 | Pflaum | |
| 6,453,008 B1 | 9/2002 | Sakaguchi et al. | |
| 2002/0085664 A1 | 7/2002 | Bromberg et al. | |
| 2002/0097320 A1 | 7/2002 | Zalis | |

(Continued)

OTHER PUBLICATIONS

F. Rashid-Farrokhi et al., "Local Tomography in Fan-Beam Geometry Using Wavelets," IEEE, 1996, 0-7803-3258-X/96, pp. 709-712.

*Primary Examiner*—Chih-Cheng G Kao
(74) *Attorney, Agent, or Firm*—Jason K. Klindtworth

(57) ABSTRACT

A CT detector includes a first detector configured to convert radiographic energy to electrical signals representative of energy sensitive radiographic data and a second detector configured to convert radiographic energy to electrical signals representative of energy sensitive radiographic data and positioned to receive x-rays that pass through the first detector. A logic controller is electrically connected to the first detector and the second detector and is configured to receive a logic output signal from the second detector indicative of an amount of a saturation level of the first detector, compare the logic output signal to a threshold value, and output, based on the comparison, electrical signals from the first detector, the second detector, or a combination thereof to an image chain.

24 Claims, 19 Drawing Sheets

U.S. PATENT DOCUMENTS

| | | |
|---|---|---|
| 2003/0021379 A1* | 1/2003 | Klotz et al. ............ 378/154 |
| 2003/0023163 A1 | 1/2003 | Johnson et al. |
| 2003/0113267 A1 | 6/2003 | Knopp et al. |
| 2003/0169847 A1 | 9/2003 | Karellas et al. |
| 2004/0136491 A1 | 7/2004 | Iatrou et al. |
| 2004/0202283 A1 | 10/2004 | Okumura et al. |
| 2004/0264627 A1 | 12/2004 | Besson |

* cited by examiner

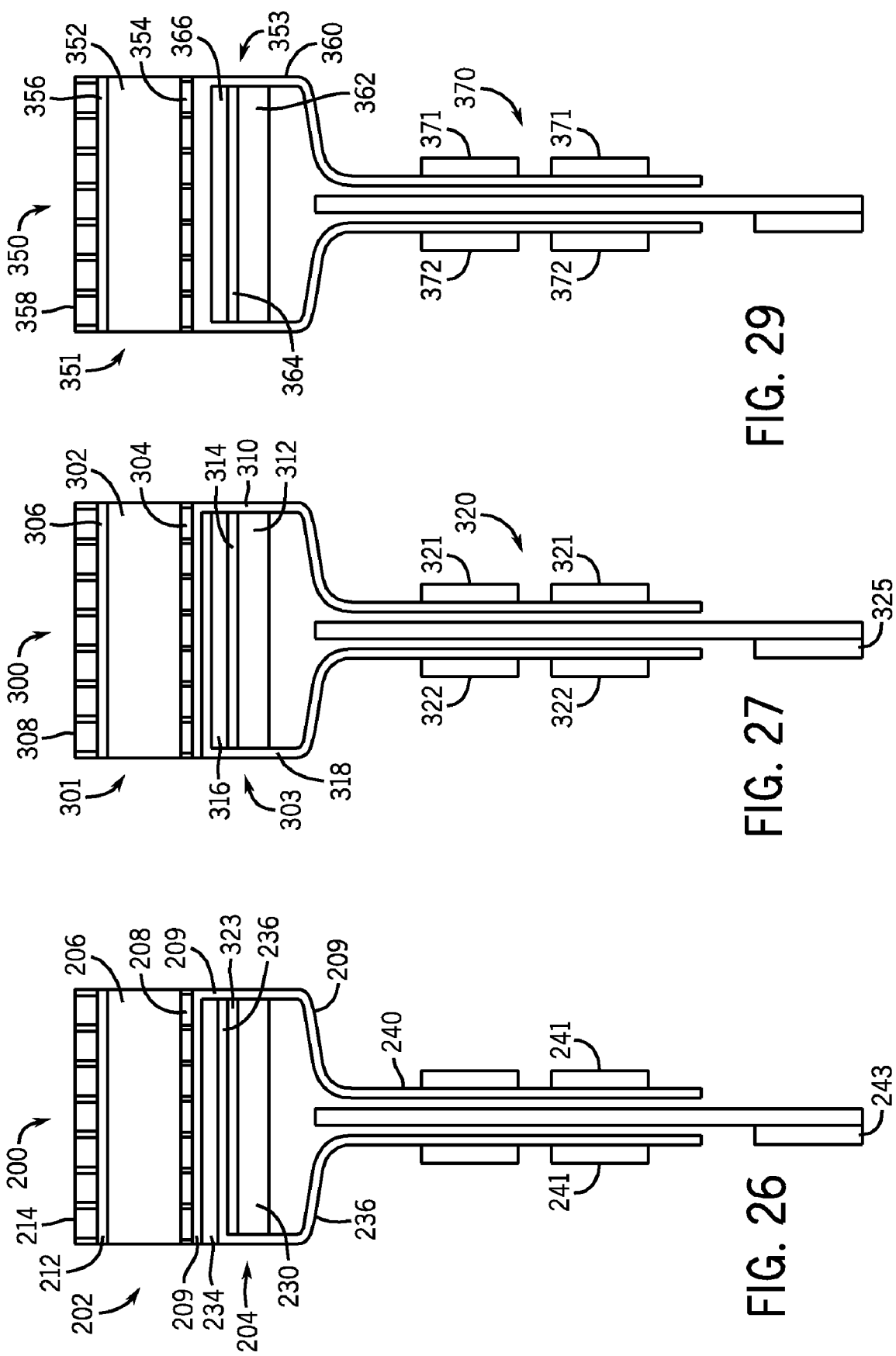

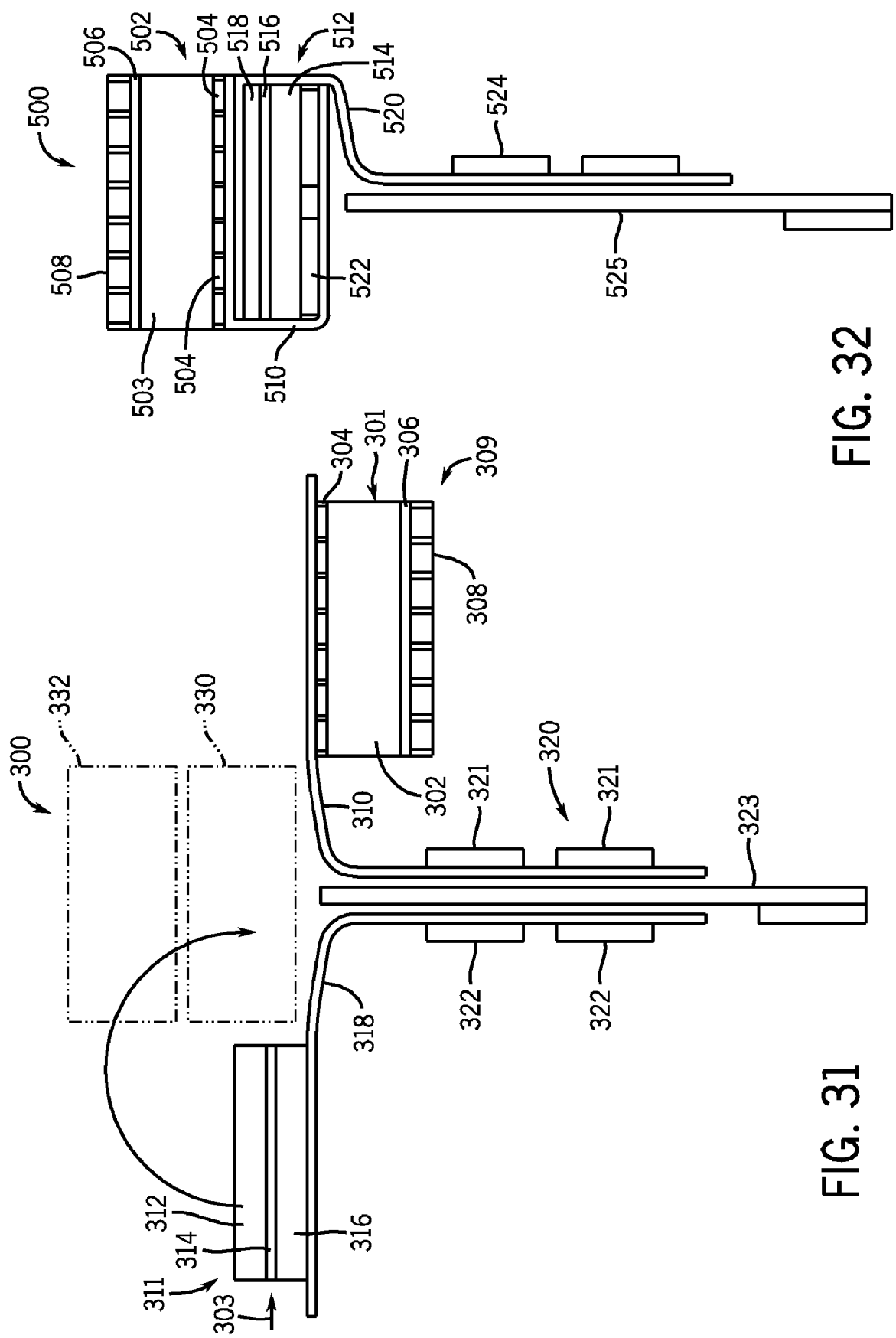

_US 7,606,347 B2_

PHOTON COUNTING X-RAY DETECTOR WITH OVERRANGE LOGIC CONTROL

CROSS-REFERENCE TO RELATED APPLICATION

The present application is a continuation in part of and claims priority of U.S. patent application Ser. No. 10/939,787 filed Sep. 13, 2004, the disclosure of which is incorporated herein.

BACKGROUND OF THE INVENTION

The present invention relates generally to diagnostic imaging and, more particularly, to a stacked detector having a logic control to select data usage of a pair of detectors.

Typically, in radiographic imaging systems, such as x-ray and computed tomography (CT), an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

In other typical radiographic imaging systems, positron emission tomography (PET) or single photon emission computed tomography (SPECT) a radiation source within the imaged object emits x-rays which are intercepted by a photon counting, energy sensitive x-ray detector. A CT system can be paired with a PET or SPECT system to produce a fused system (CT/SPECT or CT/PET) providing images indicating both anatomical structure and physiologically significant (i.e. functional) information. Such combined systems include a source that emits x-rays toward a x-ray detector and separate SPECT or PET detector which measures x-rays emitted from radiation source within the object.

In some CT imaging systems, for example, the x-ray source and the detector array are rotated within a gantry and within an imaging plane around the subject. X-ray sources for such CT imaging systems typically include x-ray tubes, which emit the x-rays as a fan beam emanating from a focal point. X-ray detectors for such CT imaging systems typically are configured in an circular arc centered to the focal spot. In addition, such detectors include a collimator for collimating x-ray beams received at the detector with focus to the focal spot. In addition, such detectors include a scintillator for converting x-rays to light energy adjacent the collimator, and a photodiode for receiving the light energy from an adjacent scintillator and producing electrical signals therefrom. Typically, each scintillator of a scintillator array converts x-rays to light energy. Each photodiode detects the light energy and generates a corresponding electrical signal as a function of the light emitted by a corresponding photodiode. The outputs of the photodiodes are then transmitted to the data processing system for image reconstruction.

In some SPECT and PET systems, for example, the one or more flat detector arrays is rotated within a gantry and within an imaging plane and around the subject. X-ray radiation sources within the imaged object emit photons in random directions. A x-ray detector typically includes a collimator for collimating x-ray beams received at the detector with focus for parallel rays contained within the imaging plane and perpendicular to the detector plane. In addition, such detectors include a scintillator for converting x-rays to light energy adjacent the collimator, and a photomultiplier tube for receiving the light energy from an adjacent scintillator and producing electrical signals therefrom which are then transmitted to the data processing system for image reconstruction.

Conventional CT imaging systems utilize detectors that convert radiographic energy into current signals that are integrated over a time period, then measured and ultimately digitized. A drawback of such detectors however is their inability to provide data or feedback as to the number and/or energy of photons detected. That is, conventional CT detectors have a scintillator component and photodiode component wherein the scintillator component illuminates upon reception of radiographic energy and the photodiode detects illumination of the scintillator component and provides an electrical signal as a function of the intensity of illumination. While it is generally recognized that CT imaging would not be a viable diagnostic imaging tool without the advancements achieved with conventional CT detector design, a drawback of these detectors is their inability to provide energy discriminatory data or otherwise count the number and/or measure the energy of photons actually received by a given detector element or pixel. That is, the light emitted by the scintillator is a function of the number of x-rays impinged as well as the energy level of the x-rays. Under the charge integration operation mode, the photodiode is not capable of discriminating between the energy level or the photon count from the scintillation. For example, two scintillators may illuminate with equivalent intensity and, as such, provide equivalent output to their respective photodiodes. Yet, the number of x-rays received by each scintillator may be different as well as the x-rays intensity, but yield an equivalent light output.

A typical PET or SPECT system uses a photon counting, energy discriminating detector constructed from a scintillator and photomultiplier tube. Such detectors have large detector elements and as such are not readily adapted to CT applications requiring high resolution imaging to capture anatomical detail in the imaged object. Accordingly, recent detector developments have included the design of an energy discriminating, direct conversion detector that can provide photon counting and/or energy discriminating feedback with high spatial resolution. In this regard, the detector can be caused to operate in an x-ray counting mode, an energy measurement mode of each x-ray event, or both.

Energy discriminating, direct conversion detectors are capable of not only x-ray counting, but also providing a measurement of the energy level of each x-ray detected. Consequently, such a detector could potentially be used for SPECT or PET imaging. While a number of materials may be used in the construction of a direct conversion energy discriminating detector, semiconductors such as Cadmium Zinc Telluride (CZT), Cadmium Telluride (CdTe) and the like have been shown to be preferred materials.

Generally, in order to create an image using a direct conversion detector, either charge integration or charge pulse counting electronics are employed. For charge integration, the charge is integrated over the area of the pixel and the integrated charge is used to generate a digital signal indicative of total x-ray count and the energy level of each x-ray detected. For pulse counting, the amplitude of the current pulse is compared to a threshold level and stored in bin counters in order to record photon energy.

A drawback of direct conversion semiconductor detectors, however, is that these types of detectors cannot count at the x-ray photon flux rates typically encountered with conventional CT systems, e.g. at or above 5-100 million counts per sec per millimeter squared (Mcps). The very high x-ray photon flux rate, above 5-100 Mcps, causes pile-up and polarization which ultimately leads to detector saturation. That is, these detectors typically saturate at relatively low x-ray flux level thresholds. Above these thresholds, the detector response is not predictable or has degraded dose utilization. For SPECT and PET, imaging flux levels are below 5-100 Mcps and such saturation in a semiconductor detector for SPECT and PET is not a practical concern. However, for CT, saturation can occur at detector locations wherein small subject thickness is interposed between the detector and the radiographic energy source or x-ray tube. It has been shown that these saturated regions correspond to paths of low subject thickness near or outside the width of the subject projected onto the detector fan-arc. In many instances, the subject is more or less circular or elliptical in the effect on attenuation of the x-ray flux and subsequent incident intensity to the detector. In this case, the saturated regions represent two disjointed regions at extremes of the fan-arc. In other less typical, but not rare instances, saturation occurs at other locations and in more than two disjointed regions of the detector. In the case of an elliptical subject, the saturation at the edges of the fan-arc is reduced by the imposition of a bowtie filter between the subject and the x-ray source. Typically, the filter is constructed to match the shape of the subject in such a way as to equalize total attenuation, filter and subject, across the fan-arc. The flux incident to the detector is then relatively uniform across the fan-arc and does not result in saturation. What can be problematic, however, is that the bowtie filter may not be optimal given that a subject population is significantly less than uniform and not exactly elliptical in shape. In such cases, it is possible for one or more disjointed regions of saturation to occur or conversely to over-filter the x-ray flux and create regions of very low flux. Low x-ray flux in the projection will ultimately contribute to noise in the reconstructed image of the subject.

Detector saturation causes loss of imaging information and results in artifacts in x-ray projection and CT images. In addition, hysteresis and other non-linear effects occur at flux levels near detector saturation as well as flux levels over detector saturation. Direct conversion detectors are susceptible to a phenomenon called "polarization" where charge trapping inside the material changes the internal electric field, alters the detector count and energy response in an unpredictable way, and results in hysteresis where response is altered by previous exposure history. In particular, photon counting, direct conversion detectors, saturate due to the intrinsic charge collection time (i.e. dead time) associated with each x-ray photon event. Saturation will occur due to pulse pile-up when x-ray photon absorption rate for each pixel is on the order of the inverse of this charge collection time. The charge collection time is approximately proportional to thickness of the direct conversion layer for a fixed electric field and anode contact size; therefore, an increase in saturation rate is possible if the direct conversion layer is thinner. However, a sufficient thickness is required to stop almost all the x-rays. Incomplete collection of x-rays results in reduced image quality, i.e. a noisy image, and poor utilization of dose to the imaged object.

An additional factor in the charge collection time is the voltage applied across the layer thickness. A larger electric field (voltage/thickness) results in inverse proportionally smaller charge collection times and proportionally larger saturate rates. However, there is a reliability issue to routing of high voltage signals. Higher reliability can be obtained for lower voltages across smaller thicknesses of direct conversion layer. However, again, a sufficient thickness of the layer is required to sufficiently stop a majority of the x-rays.

Other types of detectors in addition to direct conversion detectors also saturate. A common example is the scintillator-photodiode arrangement connected to an integrating preamplifier. Charge created from each photon is routed to the preamplifier. As x-ray flux increases, the current to the preamplifier or total charge built up over an integration time period will increase. The readout electronics have a limiting current or charge capability before saturating the amplifier. Amplifier saturation is associated with non-linear response and the loss of signal charge. This again results in poor dose utilization and image artifacts.

Another detector construction is a scintillator over photodiode connected to photon counting readout electronics. Similar constructions utilize a scintillator over avalanche-photodiode or photo-multiplier tube. Saturation of the x-ray flux rate in these photon-counting cases is also related to a dead time for clearing the charge before arrival of the next x-ray photon.

For photon counting, direct conversion detectors, a practical solution to x-ray flux rate saturation in imaging systems using x-ray sources operating above the saturation point is not known. For these systems, a total thickness of the x-ray absorbing layer may be greater than, for instance, 1.0 mm. The higher the energy of the x-rays; the higher the required thickness to sufficiently stop a predominance of the x-ray flux. A typical target value is to stop 90-99% of the incident x-rays. For Cadmium Zinc Telluride (CZT) or Cadmium Telluride (CdTe), two possible direct conversion materials used for x-ray spectroscopy, the thickness for diagnostic radiology and CT imaging is approximately 3.0-5.0 mm in order to stop most of the x-rays generated from a source at 100-200 kVp. For CZT and CdTe, the saturation limit of roughly $5\text{-}100\times10^6$ x-rays/sec/mm2 is generally found for pixel size on the order of 1.0 mm and thicknesses of order 3.0-5.0 mm. This limit is directly related to the charge collection time for CZT. Higher flux rates are theoretically possible using smaller pixels. Each pixel has a size-independent count rate limit set by the charge collection time. The saturation flux rate is set by the count rate limit divided by the area of the pixel. Therefore, the saturation flux rate increases as the pixel size decreases. Smaller pixels are also desirable because they make available higher spatial resolution information which can result in high resolution images. However, small pixel size results in higher cost and there are more channels per unit area which need to be connected to readout electronics.

In addition, smaller pixels or detector elements have larger perimeter to area ratios resulting in more cross-talk. The perimeter is a region where charge is shared between two or more pixels (i.e. cross-talk). This sharing of charge results in incomplete energy information and/or a miscount of x-ray photons because the readout electronics are not configured to combine simultaneous signals in neighboring pixels. Very high flux rates are possible with thin, photon counting, direct conversion silicon layers with pixel size <0.1 mm, but there is not sufficient stopping power in these thin layers to stop the x-rays. For integrating detectors, the size of the detector pixel and design of the preamplifier are balanced to handle an x-ray flux rate expected during imaging. For CT, the flux rate capability of the detector with integrating electronics is generally of the order $10^9$ photons/sec/mm². For x-ray projection imagers operating with charge storage, integrating detectors, the flux rate capability is only of the same order. For photon counting detectors using scintillators and one of photodiodes/APDs/photomultipliers, the dead time of the x-ray conversion layer is very fast and the dead time is usually related to the bandwidth of the electronic readout, which can also be relatively high. The problem with these detectors is varied. In the case of a photodiode, the electronic gain is not sufficient to overcome the electronic noise. In the case of APDs, there is additional gain but with associated gain-instability noise, temperature sensitivity and reliability issues. In the case of photomultiplier tubes, these devices are too large and costly for high resolution detectors covering large areas.

Detector saturation can affect image quality by constraining the number of photons used to reconstruct the image and introducing image artifacts. A minimum image quality, therefore a minimum flux rate, is required to make use of the images. In this regard, when setting the configuration of the system such that sufficient flux is received at one area of the detector, then it is likely that another area of the detector will receive higher flux, and possibly, high enough to saturate the detector in this area. Higher flux in these other areas is not necessary for the image quality; however, the loss of data due to detector saturation may need to be addressed through correction algorithms in order to reduce image artifacts. For CT imaging, the reconstruction is not tolerant to missing or corrupted data. For example, if the center of the detector is illuminated with a minimum flux for image quality purposes, and if the illuminated object is compact, then detector cells at and beyond the periphery of the object's shadow can be saturated due to thin object thickness in these projected directions. The reconstruction of the data set with these uncorrected saturated values will cause severe artifacts in the image.

A number of imaging techniques have been developed to address saturation of any part of the detector. These techniques include maintenance of low x-ray flux across the width of a detector array, for example, by using low tube current or current that is modulated per view. However, this solution leads to increased scanned time. That is, there is a penalty that the acquisition time for the image is increased in proportion to the nominal flux needed to acquire a certain number of x-rays that meet image quality requirements.

With respect to combined CT and SPECT or CT and PET imaging, the availability of an energy discriminating detector with high flux rate capability provides the opportunity for a shared detector. The x-ray photon energies of SPECT are similar to those in CT, such that a semiconductor layer thickness can be designed to meet the requirements of both CT and SPECT. However, for PET, the photon energies are at 511 eV, about 5 times higher than that used for CT and SPECT.

In a typical imaging application, x-rays are absorbed in the direct conversion material which results in creation of an electrical charge in the direct conversion material. In order to create digital image information, the charge generated is collected on the segmented anodes typically using either charge integration or charge pulse counting electronics.

One drawback of direct conversion semiconductor detectors, however, is that x-rays absorbed in the direct conversion material near the gaps or perimeters of the anodes can result in a charge being generated therein that is shared by at least two neighboring pixel anodes. When using charge integration electronics, charge sharing can manifest itself as crosstalk between neighboring pixels, thus rendering the electronics susceptible to electronic noise amplification and spatially blurring of the image. When using pulse counting electronics, charge sharing can result in dividing the charge between at least two anodes, resulting in lost counts when the amplitude of the charge pulse collected in at least one of the anodes is below a discrimination threshold. Additionally, when pulse counting, high energy x-rays can result in loss of detection quantum efficiency (DQE) by the creation of two or more counts being collected in two or more neighboring anodes, thus mis-counting the events and binning for instance a single high energy event as two or more low-energy events.

Another drawback of direct conversion semiconductor detectors is that the response at the edge and corners of the direct conversion crystal may not be not reproducible. Such locations of a direct conversion crystal typically have charge trapping centers that cause changes in the internal electric field as the incident x-ray flux changes. The changing internal field can cause a poor detector response that can lead to image quality problems.

A number of techniques have been developed to address charge-sharing in direct conversion detectors. Energy discriminating detectors typically comprise a number of segmented anodes of typically 0.2-2.0 mm that define a pixelated structure onto which the direct conversion material is electrically attached. The anodes define the response area of the imaging pixels which segment the area of the detection plane. Smaller pixels are generally desirable because they make available higher spatial resolution information which can result in higher resolution images, and because the flux rate capability is generally improved with smaller pixels. However, smaller pixel size can result in higher cost because there are more channels per unit area which need to be connected to readout electronics. In addition, smaller pixels or detector elements have larger perimeter to area ratios resulting in a larger percentage of charge sharing regions per unit area of the detector.

Because the perimeter is the region where a charge may be shared between two or more pixels, incomplete energy information and/or a miscount of x-ray photons occurs because the readout electronics are not configured to combine near-simultaneous signals in neighboring pixels. Readout electronics could incorporate a time-coincidence circuit configured to identify events occurring within a defined time window that, once identified, prevents the detected event from receiving a bin count. However, such electronics can be costly and difficult to implement.

To solve the problem regarding the reproducibility of the response at the edge and corners of the direct conversion crystal, a guard ring is typically placed on the anode surface of the device or on side walls of the crystal walls. However, a guard ring does not prevent trapping of charge within the semiconductor and does not prevent a changing electric field from developing within the semiconductor.

It would therefore be desirable to design a direct conversion, energy discriminating CT detector that can produce images above x-ray photon flux rates that typically cause saturation within a direct conversion detector. It would be further desirable to design an x-ray management system that accommodates variations in x-ray flux across a CT detector assembly and compensates for over-ranging or saturating detectors, and precludes charge-sharing within a direct conversion detector. Such a detector and flux management system would allow the use of the same detector for both CT and SPECT imaging.

BRIEF DESCRIPTION OF THE INVENTION

The present invention is directed to a multilayer CT detector that performs at very high count rates that overcomes the aforementioned drawbacks.

A CT detector capable of energy discrimination, energy integration, and direct conversion is disclosed. Also, a dual-modality detector capable of both CT and single photon emission computed tomography (SPECT) detection is disclosed. The detector includes multiple layers of semiconductor material. In this regard, the detector is constructed to be segmented in the x-ray penetration direction to optimize count rate performance as well as avoid saturation. Additionally, the CT detector may be fabricated so as to have multiple detector elements or sub-pixels per contact area. In this regard, a dynamic and flexible combining of the outputs of the individual detector elements can be carried out to inhibit use of data from a saturated detector element.

The CT detector supports not only x-ray photon counting, but energy measurement or tagging as well. As a result, the present invention supports the acquisition of both anatomical detail as well as tissue characterization information. In this regard, the energy discriminatory information or data may be used to reduce the effects of beam hardening and the like. Further, these detectors support the acquisition of tissue discriminatory data and therefore provide diagnostic information that is indicative of disease or other pathologies. For example, detection of calcium in a plaque in a view is possible. This detector can also be used to detect, measure, and characterize materials that may be injected into a subject such as contrast agents and other specialized materials such as targeting agents. Contrast materials can, for example, include iodine that is injected into the blood stream for better visualization.

Therefore, in accordance with one aspect of the present invention, a CT detector includes a first detector configured to convert radiographic energy to electrical signals representative of energy sensitive radiographic data and a second detector configured to convert radiographic energy to electrical signals representative of energy sensitive radiographic data and positioned to receive x-rays that pass through the first detector. A logic controller is electrically connected to the first detector and the second detector and is configured to receive a logic output signal from the second detector indicative of an amount of a saturation level of the first detector, compare the logic output signal to a threshold value, and output, based on the comparison, electrical signals from the first detector, the second detector, or a combination thereof to an image chain.

In accordance with another aspect, a radiographic imaging system includes a radiation source configured to project x-rays toward a subject to be scanned, a detector assembly comprising a first detector layer and a second detector layer, the second layer positioned to receive x-rays from the radiation source that pass through the first detector layer, each of the first and second layers configured to receive x-rays projected from the radiation source and convert radiographic energy to electrical signals representative of energy sensitive radiographic data, and a device configured to receive data indicative of a flux rate in at least one of the first and second detector layers, determine whether to output electrical signals in the first detector layer for image reconstruction based on the received data, and determine whether to output electrical signals in the second detector layer for image reconstruction based on the received data.

According to another aspect, a method of fabricating an imaging system includes providing an x-ray source, positioning a first detector to receive x-rays that emit from the x-ray source, positioning a second detector to receive x-rays that emit from the x-ray source and that pass through the first detector, and electrically coupling a logic device to the first and second detectors, the logic device configured to indicate a level of x-ray flux in one of the first and second detectors.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 26 is a section view of the detector module of FIG. 24 taken along line 26-26.

FIGS. 27-30 are section views of alternative detector modules embodiments according to an embodiment of the present invention.

FIG. 31 is a schematic diagram showing an assembly procedure of a detector module according to an embodiment of the present invention.

FIGS. 32-36 are section views of alternative detector modules according to embodiments of the present invention.

DETAILED DESCRIPTION OF THE PREFERRED EMBODIMENT

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
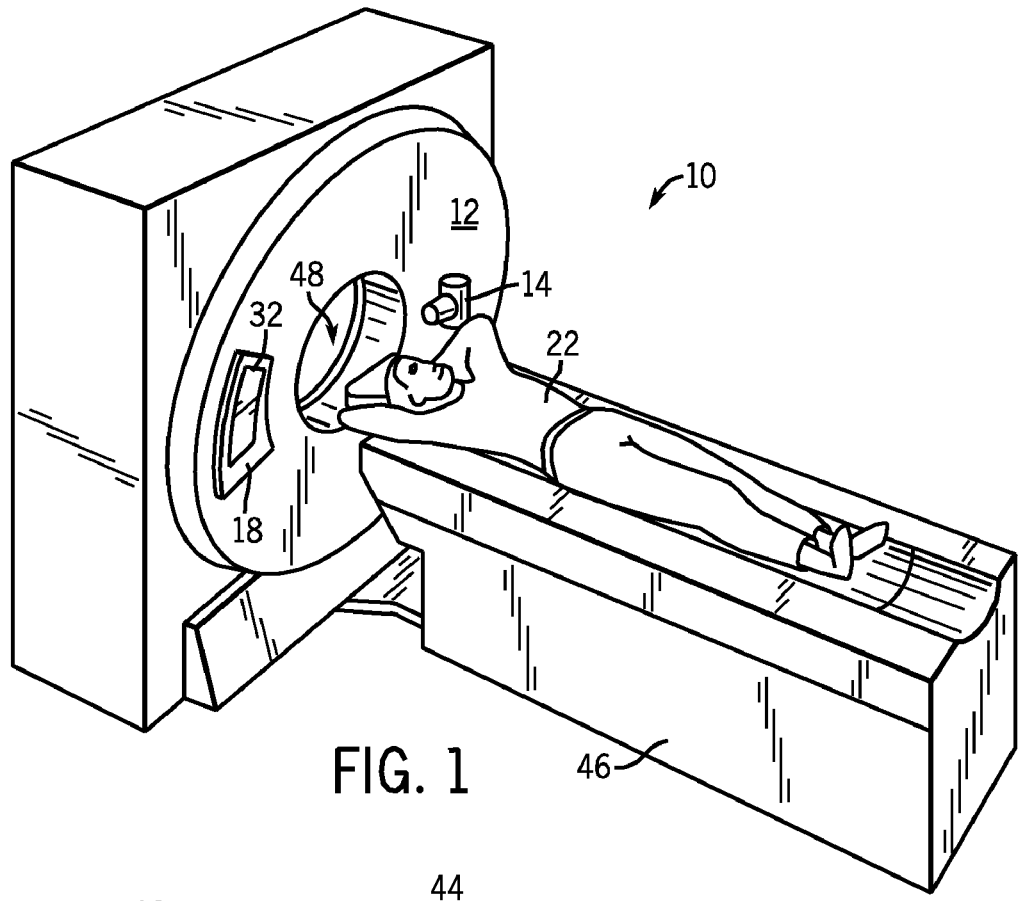
FIG. 1 is a pictorial view of a CT imaging system.
Figure 2:
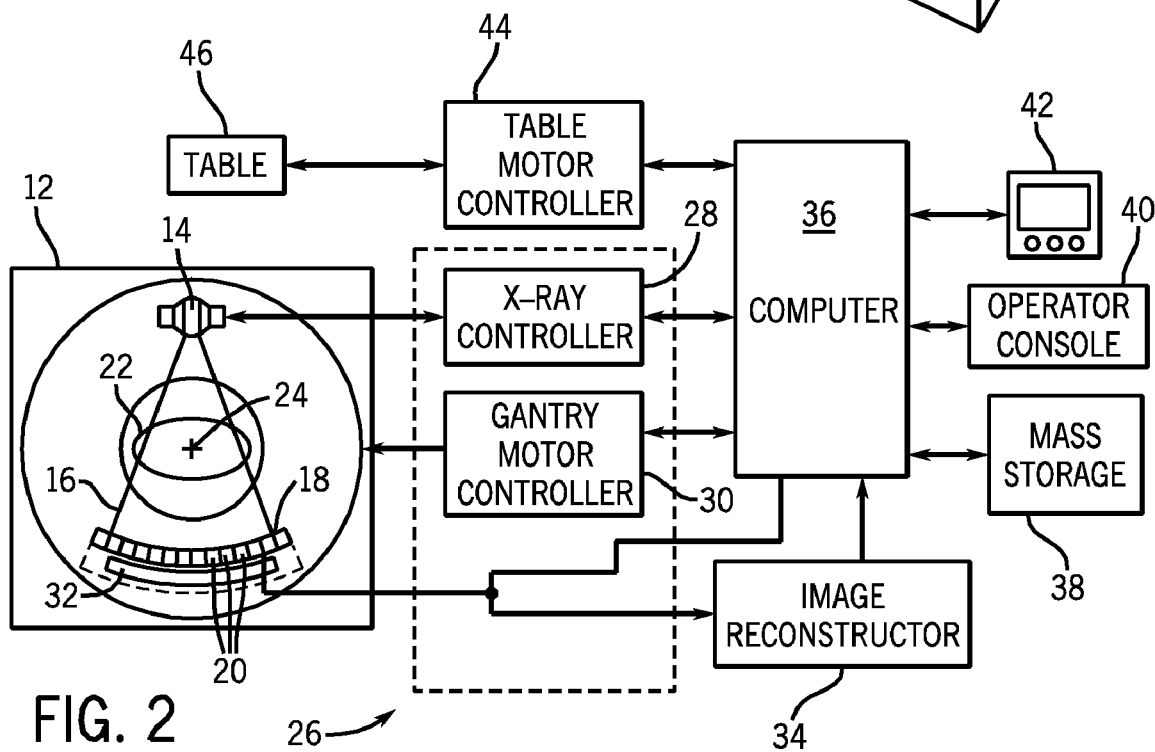
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
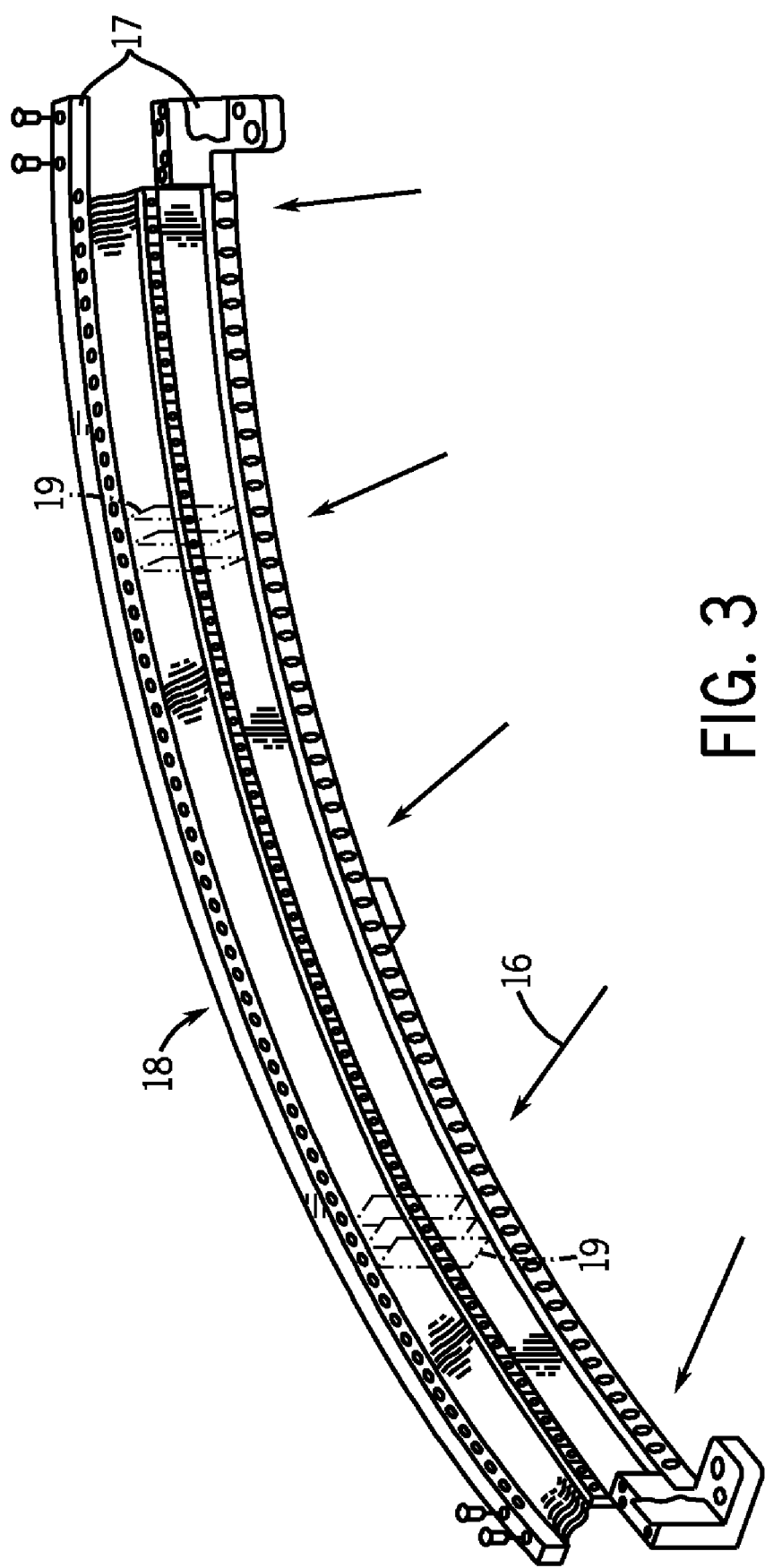
FIG. 3 is a perspective view of one embodiment of a CT system detector assembly.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
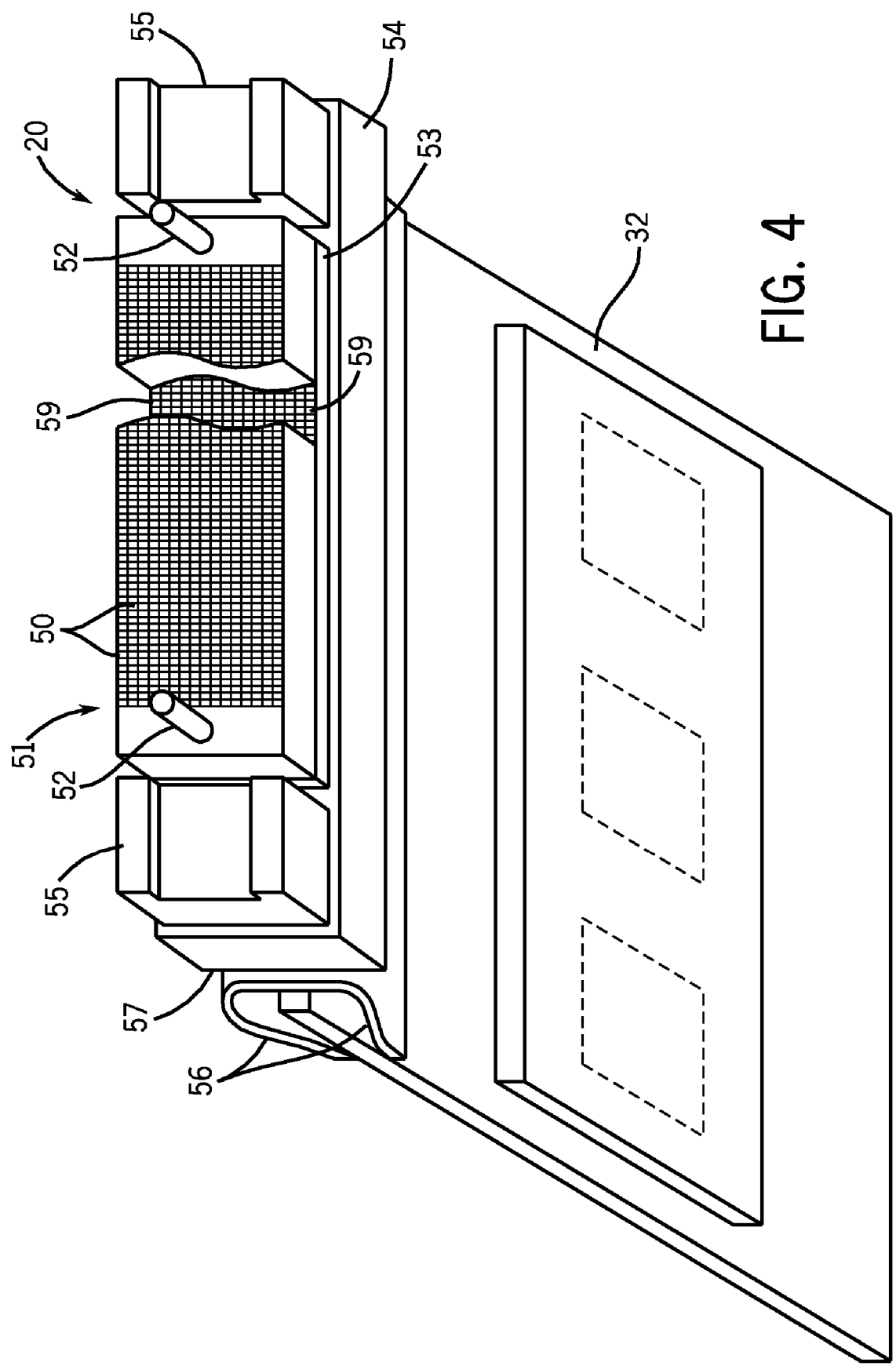
FIG. 4 is a perspective view of a CT detector incorporating the present invention.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 is designed to directly convert radiographic energy to electrical signals containing energy discriminatory or photon count data. The present invention contemplates a number of configurations for these detectors, its components, and the manner in which data is read out. Notwithstanding the distinctions between each of these embodiments, each detector does share two common features. One of these features is the multilayer arrangement of semiconductor films or layers. In a preferred embodiment, each semiconductor film is fabricated from Cadmium Zinc Telluride (CZT). However, one skilled in the art will readily recognize that other materials capable of the direct conversion of radiographic energy may be used. The other common feature between the various embodiments is the use of interstitial or intervening metallized films or layers separating the semi-conducting layers. As will be described, these metallized layers are used to apply a voltage across a semiconductor layer as well as collect electrical signals from a semiconductor layer. As will also be described, detectors with such a design have improved saturation characteristics and photon count fidelity.

It is generally well known that the charge collection time of a semiconductor layer is inversely related to the maximum periodic count rate saturation threshold (MPR) of the layer. A thinner layer will have faster collection of charges and higher MPR. However, the thinner layer will stop a smaller fraction of the incident x-rays. The charge collection time is approximately proportional to a dimension d, which is the smaller of either the thickness of the detector or the pixel contact size, whereas the radiographic energy deposition efficiency is exponentially increasing with thickness. The count rate performance for a CZT detector may be defined by:

$$MPR = \frac{\mu_e E}{d}.$$

From this definition, assuming an equal contact size and thickness of d=0.3 cm and an electric field E of 1000 V/cm, and with a $\mu_e$ of about 1000 cm$^2$/(V sec), a maximum periodic count rate of 3.0 megacounts/sec may be achieved. Since the arrival of x-rays is not periodic but random, significant saturation effects will occur at 10× lower average rate. In other words, the count rate of a CZT semiconductor layer that is 3.0 mm thick may have a count rate performance in the range of 0.3-3.0 megacounts/sec. However, as will be described, constructing a direct conversion semiconductor detector with multiple layers with the cumulative thickness of a single thicker layer can improve count rate performance.

Moreover, thinner conversion layers not only improve count rate performance due to a reduction of charge collection time, but also provide an improvement in charge collection efficiency thereby reducing polarization, detector count and energy response fidelity. Thinner conversion layers also reduce charge sharing between pixel elements thereby improving energy discrimination performance and spatial resolution.

Improvement in flux rate performance through the segmenting of the detector into multiple thin layers can be attributed to a number of factors. First, having multiple layers divides the total flux rate among the different layers. Each layer will experience only a fraction of the total flux. For example, incomplete x-ray attenuation of the first layer, which is thin (relative to the attenuation depth of x-rays), will insure that saturation of this layer will be at a higher count rate than that of a thick layer that stops all the x-rays.

A second factor is that the thickness of the layers can be configured to insure that if one layer does saturate, another layer is non-saturated and gives valid data for that view. For example, if one of the layers is constructed such that it stops only 5% of the x-rays, then it will saturate at 20× the flux rate a thick layer designed to stop all the x-rays. A third factor is that charge collection time decreases as layer thickness and pixel size decrease. The charge collection time is approximately proportional to either the thickness or pixel contact size, whichever is smaller, divided by the mobility and electric field across the layer. Smaller thicknesses and/or pixel size gives higher flux rate limit for that layer.

A fourth factor is that thinner layers also yield a reduction in cross-talk. The impact of pixel size on cross-talk is approximately given by the effective perimeter area over the total pixel area. That is, cross-talk is scaled by a factor 4 W*aT/W$^2$ where W is the pixel pitch and aT is a charge spreading length proportional to the layer thickness. Therefore, cross-talk decreases as the layer thickness decreases. The competing effects of flux rate saturation and cross-talk can be traded off by study of their impact on the detective quantum efficiency, (DQE(f)) an important figure of merit for x-ray imaging detectors. DQE falls off as a function of count rate, less so for thinner layers. The design methodology for optimization of the number of layers and their thickness is predicated upon obtaining the greatest count rate before which the DQE(f) has decreased below any point on a certain threshold curve.

A fifth factor is the reduction in polarization due to the more efficient collection of electrons and holes. In a thinner layer, the electrons and holes are able to travel a smaller distance before being collected; therefore, the electron and holes are less susceptible to trapping.

In addition to these five factors for improved count rate limit upon use of thin layers, the flux rate limit (i.e. count rate per unit area) is improved by using smaller pixel size which is favored in thin layers because of reduced crosstalk.

Figure 5:
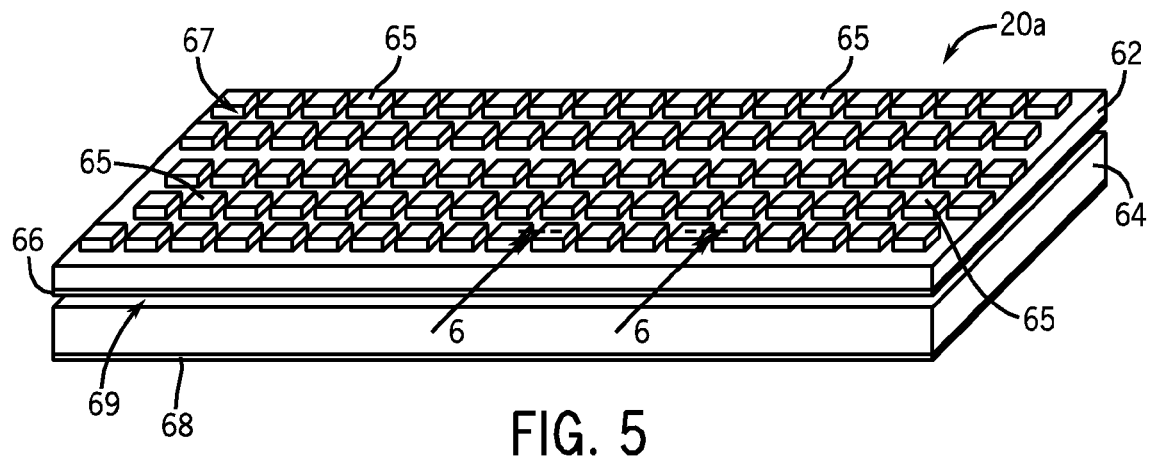
FIG. 5 is a partial perspective view of a two-layer detector in accordance with the present invention.

Referring now to FIG. 5, a portion of a two-layered CZT or direct conversion detector 20a in accordance with one embodiment of the present invention is shown in perspective. Detector 20a is defined by a first semiconductor layer 62 and a second semiconductor layer 64. During the fabrication process, each semiconductor layer 62, 64 is constructed to have a number of electronically pixelated structures or pixels to define a number of detection elements or contacts 65. This electronic pixelation is accomplished by applying a 2D array 67, 69 of electrical contacts 65 onto a layer 62, 64 of direct conversion material. Moreover, in a preferred embodiment, this pixelation is defined two-dimensionally across the width and length of each semiconductor layer 62, 64.

Detector 20a includes a contiguous high voltage electrode 66, 68 for semiconductor layers 62, 64, respectively. Each high voltage electrode 66, 68 is connected to a power supply (not shown) and is designed to power a respective semiconductor layer during the x-ray or gamma ray detection process. One skilled in the art will appreciate that each high voltage connection layer should be relatively thin so as to reduce the x-ray absorption characteristics of each connection layer and, in a preferred embodiment, is a few hundred angstroms thick. As will be described in greater detail below, these high voltage electrodes may be affixed to a semiconductor layer through a metallization process.

Figure 6:
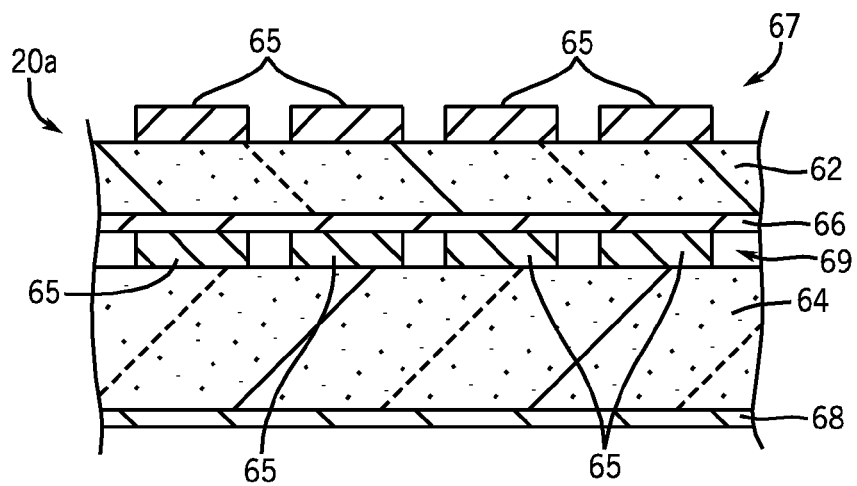
FIG. 6 is a cross-sectional view of FIG. 5 taken along lines 6-6 thereof.

Referring now to FIG. 6, a cross-sectional view of FIG. 5 taken along line 6-6 thereof illustrates the relative thickness of each semiconductor layer 62, 64 in one embodiment. In addition, for this embodiment, the pixel pitch and contact size are similar in both layers and about equal to the smaller thickness. Similarly to the high voltage electrode layers 66, 68, the 2D contact arrays 67, 69 should also be minimally absorbent of radiographic energy. Each array or signal collection layer is designed to provide a mechanism for outputting the electrical signals created by the semiconductor layers to a data acquisition system or other system electronics. As explained in more detail later, a mechanism for flexibly combining signals for pixels in different layers is provided. One skilled in the art will appreciate that many (possibly several hundred) interconnects (not shown) are used to connect all the contacts 65 with the CT system electronics. Further, the cumulative 3.0 mm thickness of the semiconductor conversion layer is such that 99% of the x-rays are absorbed. The absorption is calculated with a physics model for an x-ray spectrum typical of a medical CT acquisition, 120.0 kvp spectrum filtered by 20.0 cm.

In addition, as shown in FIG. 6, the thickness of the semiconductor layers 62, 64 is different from one another but the pixel pitch and contact size is similar. The layers are arranged with a specific order with regard to the x-ray direction so as to leverage the exponential absorption characteristic. For FIG. 6, when the x-rays are incident upward toward the bottom common contact array, more x-rays are deposited in semiconductor layer 62 than in semiconductor layer 64. For example, assuming that semiconductor layer 62 has a thickness of one millimeter (mm) and semiconductor layer 64 has a thickness of 2.0 mm, semiconductor layer 62 is expected to absorb about 92% of the x-rays whereas the second semiconductor layer 64 is expected to absorb about 7% of the x-rays. The combined total absorption for the two layers replicates the 99% efficiency of a 3.0 mm layer. One important benefit of the construction compared to 3 mm thick single layer, is a decrease in polarization effects for these two thinner layers. This benefit itself will allow operation with a tenfold increase in flux rate in most practical applications.

In addition, by combining the count response from the two layers with a specific self-correction algorithm, the segmented detector, detector 20a, may be constructed to provide a tenfold increase in count rate performance relative to a single 3.0 mm thick layer of semiconductor material. Consider, for example, a CT detector, as described herein can be constructed to have a first layer absorbing 92% of the incident x-ray flux and second layer absorbing 7%. As a result, the second layer will saturate at a flux rate at 14× higher than a 3.0 mm thick layer. As the incident flux rate increases, the second layer will saturate or over-range at an x-ray flux more than the x-ray flux required to saturate a 3.0 mm thick layer. This variability in saturation characteristics of multiple layers of a single CT detector allows for the output of an over-ranged layer to be estimated by the effective signal in a non-over-ranged or non-saturated layer. In this regard, a saturation state of a given detector layer is detected and, as a result, signal for the saturated layer, or equivalent 3.0 mm thick layer, is empirically estimated from the output of the non-saturated layer in the detector.

An example of this self-correctability algorithm is that at high count rate above which the first layer is saturated, only the count response from a second layer weighted by its fractional absorption is assigned to that projection for each pixel. At low count rate, a weighted sum of the response from both layers is assigned to the projection for each pixel. A more sophisticated algorithm may combine the signals for the two layers with weighting inverse to their DQE such that as the statistical error in one layer's value grows with increasing count rate, then its value is added to the combined sum with reduced weight.

It is contemplated that a CT detector assembly could be constructed such that each CT detector is constructed with such over-range correctability. However, it is also contemplated that only those detectors in the detector assembly typically associated with over-ranging are constructed with this over-ranging self-correctability. For instance, the periphery detectors of a detector assembly typically encounter higher flux conditions than the more centrally disposed detectors. In this regard, the peripheral detectors can be constructed with over-ranging self-correctability whereas the more centrally located detectors are not. Further, layers with other detection mechanisms and detector materials having high count rate capability, but poor count rate and/or energy response characteristics, can be used in certain parts of the detector to estimate the count rate and energy response of the saturated layer.

Additionally, it is contemplated that a given CT detector may have more than two semiconductor layers. In this regard, the effective signal output of two or more non-saturated layers could be used to estimate the output of the saturated layers. For instance, a detector may be constructed with a first layer that has a 35× effective response, the second layer having a 10× effective response, and a third layer with an effective response equivalent to that of the first layer. In this regard, the first and third layers would saturate at higher x-ray flux layers than the second layer. Accordingly, when the second layer has over-ranged or saturated, the output of the first and third layers can be used to compensate or effectively determine the output of the over-ranging second layer.

Figure 7:
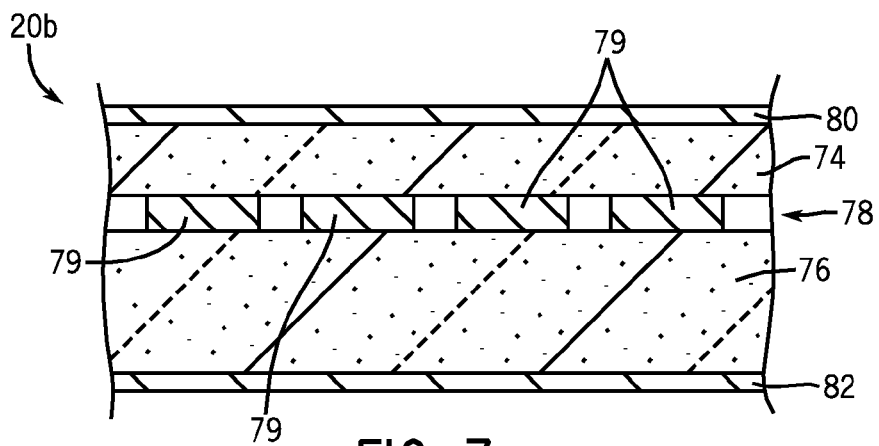
FIGS. 7-9 illustrate cross-sectional views of direct conversion detectors in accordance with several additional embodiments of the present invention.

Referring now to FIG. 7, another contemplated design for a CZT or direct conversion detector is shown. In this embodiment, detector 20b also includes a pair of semiconductor layers 74, 76. In contrast to the previously described embodiment, detector 20b includes a single, common signal collection layer or 2D contact array 78. This single, yet common array 78 is designed to collect electrical signals from both semiconductor layers 74, 76 and output those electrical signals to a DAS or other system electronics. In addition, detector 20b includes a pair of high voltage electrodes 80, 82. Each high voltage electrode effectively operates as a cathode whereas the contacts of the 2D array 78 operate as an anode. In this regard, the voltage applied via high voltage connections 80, 82 creates a circuit through each semiconductor layer to the signal collection contacts array 78.

Figure 8:
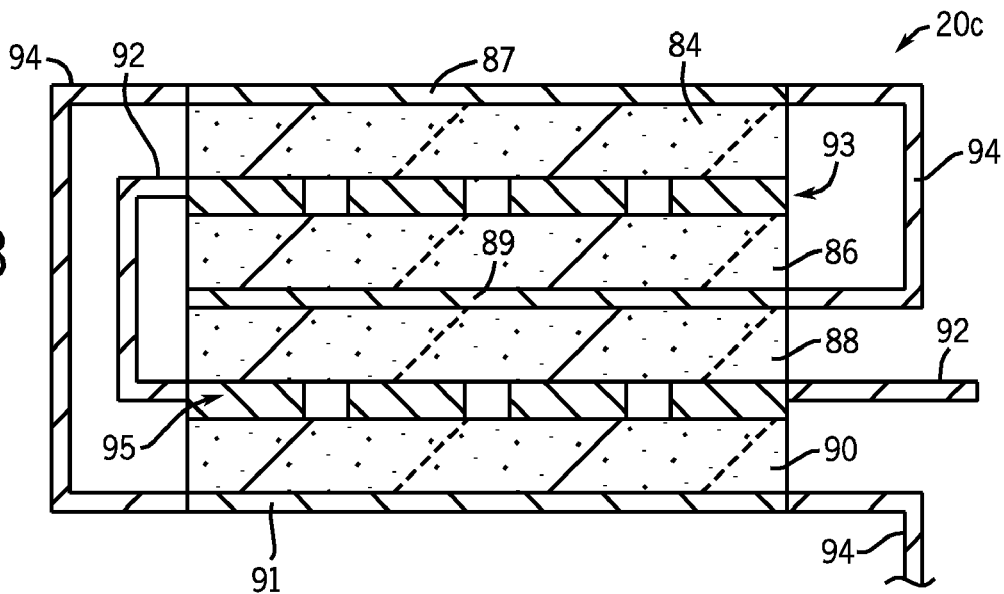

Yet another contemplated embodiment is illustrated in FIG. 8. As shown in this embodiment, detector 20c includes four semiconductor layers 84, 86, 88, and 90. Detector 20c further includes two electrically conductive lines or paths 92, 94 that are electrically connected to high voltage electrodes 87, 89, 91 as well as collection contact arrays 93, 95. Electrically conductive path 92 receives and translates electrical signals from contact arrays 93, 95. In this regard, a single data output is provided to the CT system electronics. Similar to a single signal collection lead, a single high voltage connection 94 is used to power the four semiconductor layers 84-90 via electrodes 87, 89, 91. Detector 20c only requires a single high voltage connection.

Figure 9:
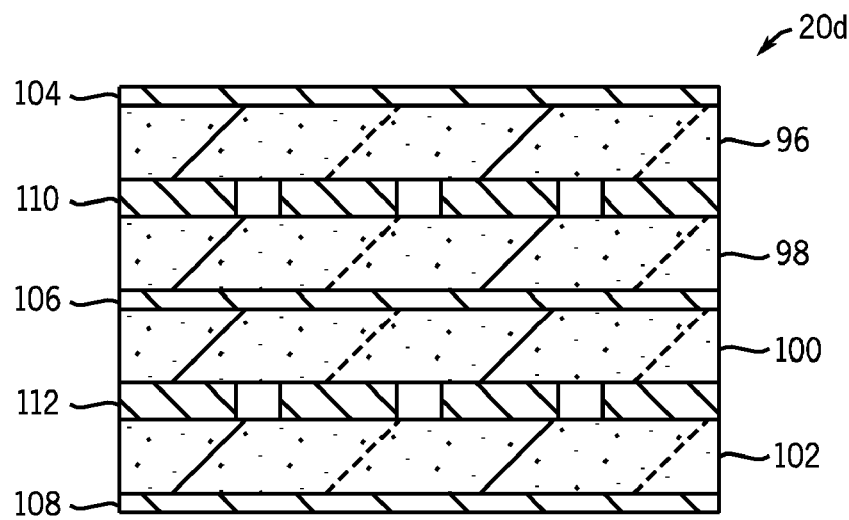

Referring to FIG. 9, a monolithic embodiment of the present invention is shown. Similar to the embodiment of FIG. 6, detector 20d includes four semiconductor layers 96-102. Each semiconductor layer 96-102 is connected to a pair of electrically conductive layers. In this regard, one electrically conductive layer is used for application of a voltage whereas the other electrically conductive layer is used for collection of the electrical signals generated by the respective semiconductor layers. To minimize the number of electrically conductive layers, detector 20d utilizes an alternating electrically conductive layer architecture. That is, every other electrically conductive layer is used for high voltage connection with the other electrically conductive layers used for signal collection. In this regard, electrically conductive layers 104, 106, and 108 are used for application of a relatively high voltage whereas layers 110 and 112 include contacts for signal collection. As such, high voltage collection layers 104 and 108 are used to apply a voltage to semiconductor layers 96 and 102, respectively. High voltage connection layer 106 is used to apply a voltage to semiconductor layers 98 and 100.

As described above, in a preferred embodiment, each semiconductor layer is constructed from CZT material. One skilled in the art will appreciate that there are a number of techniques that may be used to construct such a semiconductor. For example, molecular beam epitaxy (MBE) is one method that may be used to grow each thin layer of CZT material. Screen printing of CZT particles in polymetric binder is a potentially low cost, low temperature method of forming layers on a flexible wiring substrate. One skilled in the art will appreciate that a number of techniques may be used to metallize the semiconductor layers to provide the electrically conductive connections heretofore described.

Figure 10:
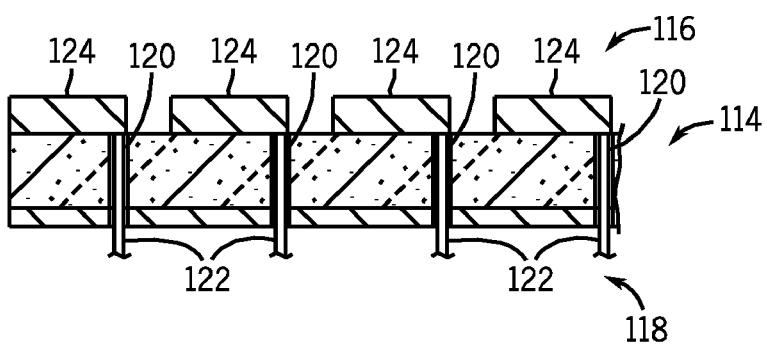
FIG. 10 is a cross-sectional view illustrating signal feedthroughs that are created in another embodiment of the invention.

Further, metallization may also be used to provide signal feedthroughs for the collection contacts as illustrated in FIG. 10. As shown, a single layer of semiconductor material 114 is sandwiched between an array 116 of collection contacts and a high voltage electrode layer 118. Prior to metallization of the semiconductor layer 114 to form collection contact array 116 and high voltage electrode layer 118, holes 120 may be etched or otherwise formed in semiconductor 114. The holes 120 may then be metallized to provide a signal feed path 122 from a respective collection contact 124. The signal feedthroughs or conductive paths 122 are constructed within holes 120 so as to not be in contact with the near-contiguous high voltage electrode layer 118. In this regard, signal runs may extend vertically or in the x-ray reception direction throughout the detector to a bus (not shown) designed to translate the electrical signals emitted by the individual collection contacts 124 to the CT system electronics. As a result, a stacked arrangement of a series of thin stacked layers in the x-ray direction is formed.

Heretofore, the present invention has been described with respect to a multilayer CT detector designed with different layer thicknesses but similar dimension of the pixel size.

The present invention has been described with respect a multi-layer CT detector incorporating direct conversion, semiconductor layers with varying thickness to reduce the likelihood of such an energy sensitive CT detector saturating or over-ranging at the x-ray flux rates typically encountered with conventional CT scans. As will be described hereinafter, however, the present invention is also directed to an energy sensitive, over-ranging resistant CT detector that utilizes variability in the electrical contacts of a multi-layer CT detector to improve saturation characteristics of the CT detector.

Figure 11:
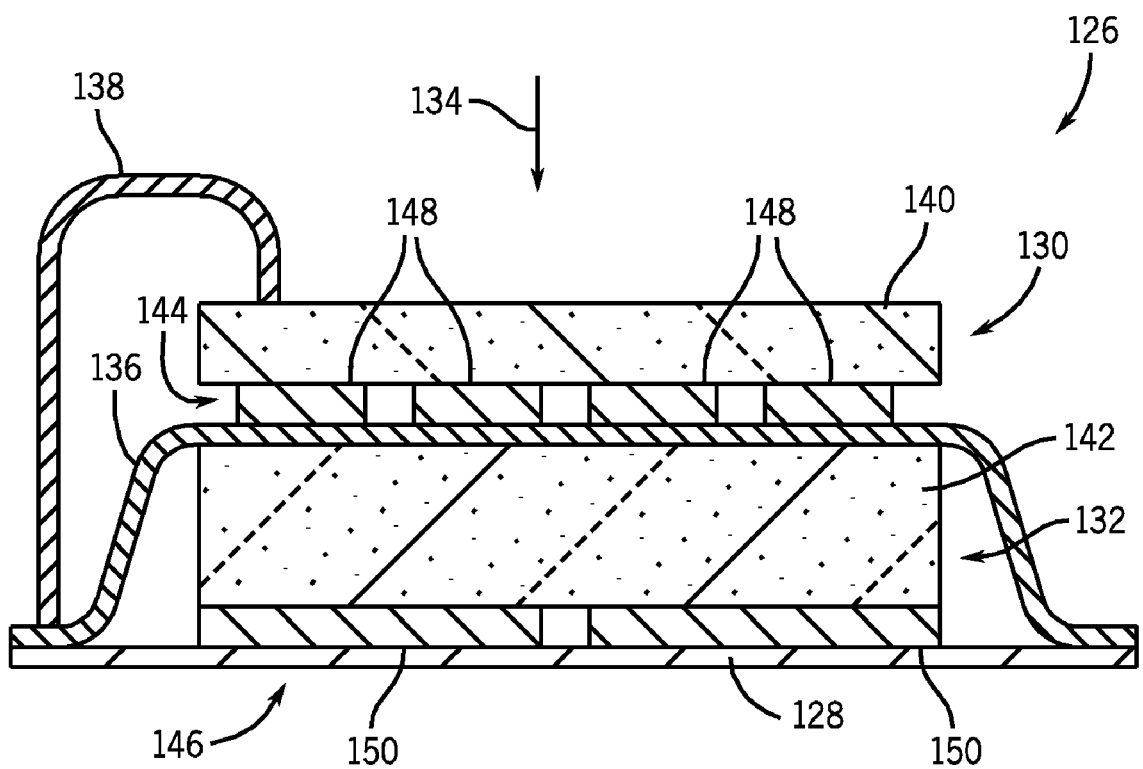
FIG. 11 is a cross-sectional schematic view of a CT detector in accordance with another embodiment of the present invention.

Referring now to FIG. 11, a side elevational, exploded view of a portion of a CT detector incorporating the present invention is shown. As shown, the detector 126 is formed on a substrate 128 that is secured to a detector frame (not shown) via fasteners (not shown). Substrate 128 supports a pair of detector layers 130 and 132. Each detector layer 130, 132 is composed of a radiation conversion component and a signal collection component. Layers 130, 132, which in the illustrated embodiment, have different thicknesses, are stacked in the x-ray direction 134 and separated from one another by a flex layer 136. The CT detector 126 also includes a high voltage bias wire 138 connected to detector layer 130 to bias the detector assembly.

As referenced above, detector 126 includes a pair of detector layers 130 and 132. The detector layers may comprise scintillator and photodiodes consistent with conventional CT detectors or fabricated from direction conversion semiconductor material, such as CZT, coupled to a number of detector elements or pixels. As illustrated in FIG. 11, detector layer 130 differs from detector layer 132 in the thickness of respective conversion components 140, 142 and the number and size of the respective detector element arrays 144, 146. As illustrated, detector element array 144 has half the pixel pitch, or four times the number of detector elements 148 than detector element array 146 for an equivalent area of the detector. Additionally, the contact area of detector elements 148 is one fourth that of detector elements 150. As will be described, this variation in the detector element arrays within a single CT detector greatly enhances the saturation characteristics of the detector.

By varying the size of the detector elements within a given detector 126, the charge collection time associated with each layer of the detector is varied. That is, one skilled in the art will readily appreciate that charge collection time decreases as the thickness of a conversion layer decreases and the size of the detector element decreases. That is, the charge collection time of a detector layer is approximately proportional to the thickness of the conversion layer or detector element size, whichever is smaller, divided by the mobility and electric field across the detector layer. The count rate saturation threshold will be larger for smaller pixel size. Furthermore, smaller pixel area implies a higher flux rate saturation threshold relative for a given count rate saturation threshold in proportion to the area reduction. As such, as conversion layer thickness and/or detector element size decreases, the flux rate limit for the corresponding detector layer increases, thereby, improving the saturation characteristics for that layer of the CT detector. This improvement and variability in saturation characteristics allows for a detector to be constructed where some layers withstand higher x-ray flux levels and provide inputs to a self-correctability algorithm.

Figure 12:
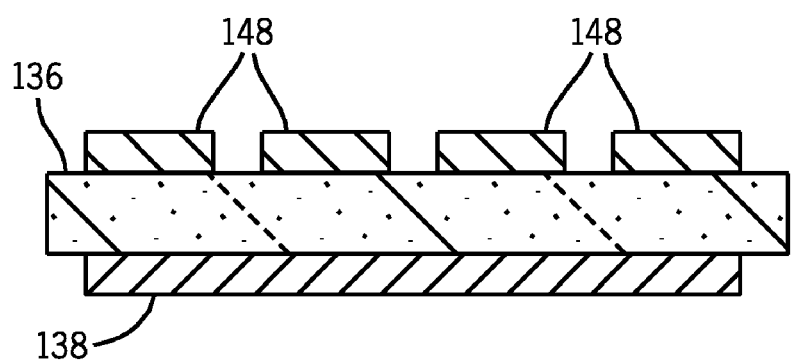
FIG. 12 is a cross-sectional view of an alternate embodiment of a portion of a CT detector according to the present invention.

In the embodiment illustrated in FIG. 11, the voltage bias wire or lead 138 extends from substrate 128 to direct conversion layer 130. It is contemplated, however, as shown in FIG. 12 that the high voltage bias wire 138 may be placed on flex layer 136. Flex layer 136 constitutes a routing layer and is used to connect the individual detector elements 148 to the readout electronics, i.e. DAS and image reconstructor, of the CT scanner 10. In the embodiment illustrated in FIG. 12, the high voltage wire 138 may be metallized on surface of flex layer 136 and the detector elements 148 may be metallized on an opposite surface.

Figure 13:
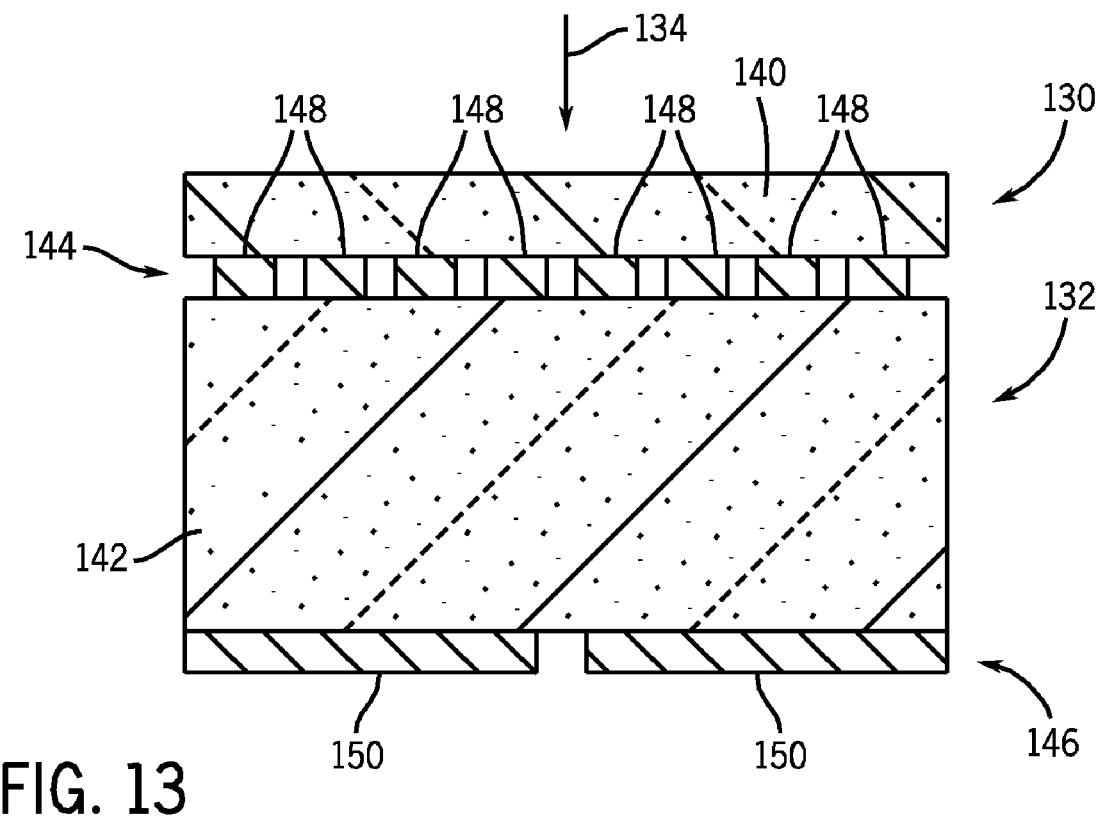
FIG. 13 is a cross-sectional view of a portion of a CT detector in accordance with yet another embodiment of the present invention.

FIG. 13 illustrates another orientation of the detector layers 130, 132 and their respective components relative to one another. As shown, the differences in thickness between direct conversion components 140 and 142 may be varied from that shown in FIG. 11 to achieve different absorption and flux rate characteristics. For example, assuming that detector elements 148 have a pixel size of 0.25 mm and detector elements 150 have a pixel size of 1.0 mm, detector layer 130, assumed to have a thickness of 0.4 mm, will stop one-half of the x-rays 134 impinged thereon and conversion layer 142, assumed to have a thickness of 4.6 mm, will stop the other half of x-rays 134 not absorbed by layer 140. The absorption is calculated with a physics model for an x-ray spectrum typical of a medical CT system, 140 kvp spectrum filtered by 3.0 cm. Relative to a single layer 5.0 mm thick, both detector layers 130, 132 will each have a two-fold improvement in flux rate capability due to incomplete absorption in each layer individually. Further, layer 130 has $\frac{1}{16}$ the area of a 1.0 mm pixel resulting in 16× higher flux rate saturation threshold versus a 1.0 mm pixel. Moreover, the combination of reduced layer thickness and reduced detector element size results in a 4× reduced charge collection time for layer 130 relative to a single 5.0 mm detector layer with 1.0 mm pixel size. The flux rate improvements due to each of these mechanisms are multiplicative. As a result, this combination of incomplete absorption (2×), smaller area (16×) and decreased charge collection time (4×), the total flux rate saturation threshold for detector layer 130 may be 128× higher relative to a 5.0 mm thick layer with 1.0 mm detector element pitch. Further, layer 130 will have less polarization due to improved charge collection efficiency in the thin layer.

Figure 14:
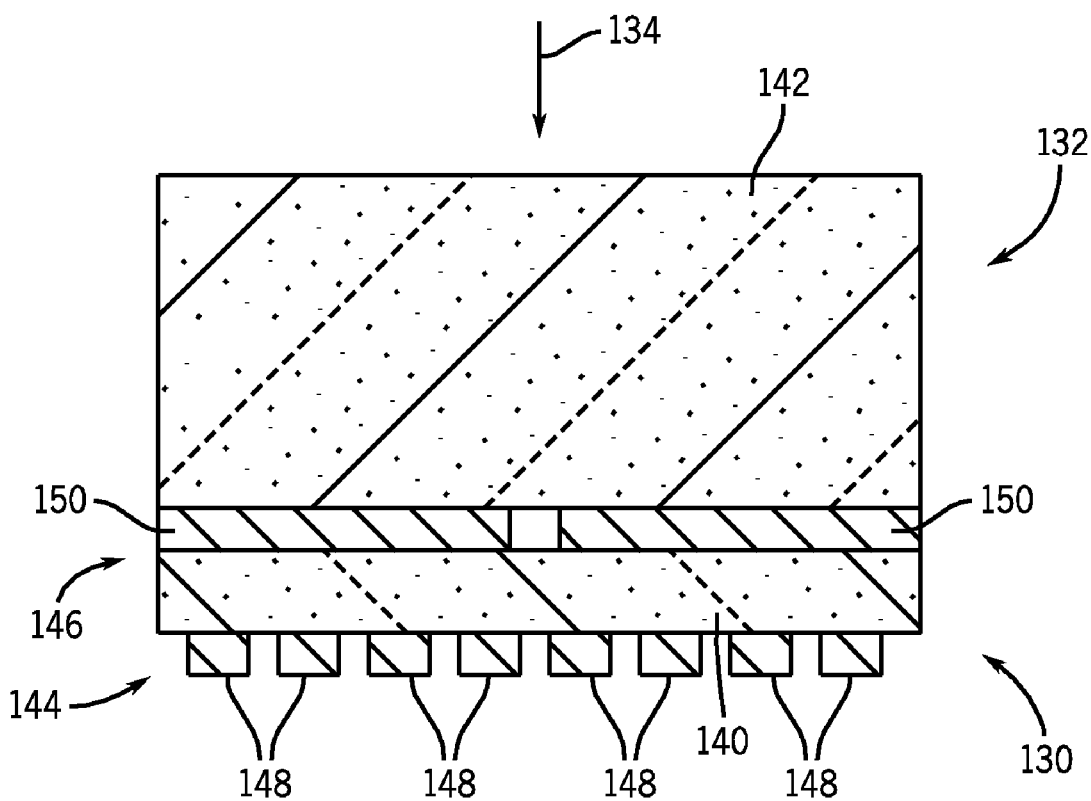
FIG. 14 is a cross-sectional view of yet another embodiment of a CT detector according to the present invention.

Referring now to FIG. 14, relative to the embodiment of FIG. 13, the order of the layered detector has been reversed. This reversal results in 99% of x-ray absorption in detector layer 132, which has a detector element pitch of 1.0 mm. As such, only 1% of the x-rays will be left for absorption in detector layer 130, which has detector element pitch of 0.25 mm. Accordingly, the absorbed flux rate fraction for detector layer 130 is 100× less than that of a single layer detector 5.0 mm thick and a pitch of 0.25 mm. Detector layer 132 achieves a 6× increase in flux rate capabilities due to 4× faster charge collection time and $\frac{1}{16}$ the pixel area. In total, the multi-layer detector has a 6400× improvement in flux rate performance compared to a single layer detector 5.0 mm thick and a detector element pitch of 1.0 mm.

Figure 15:
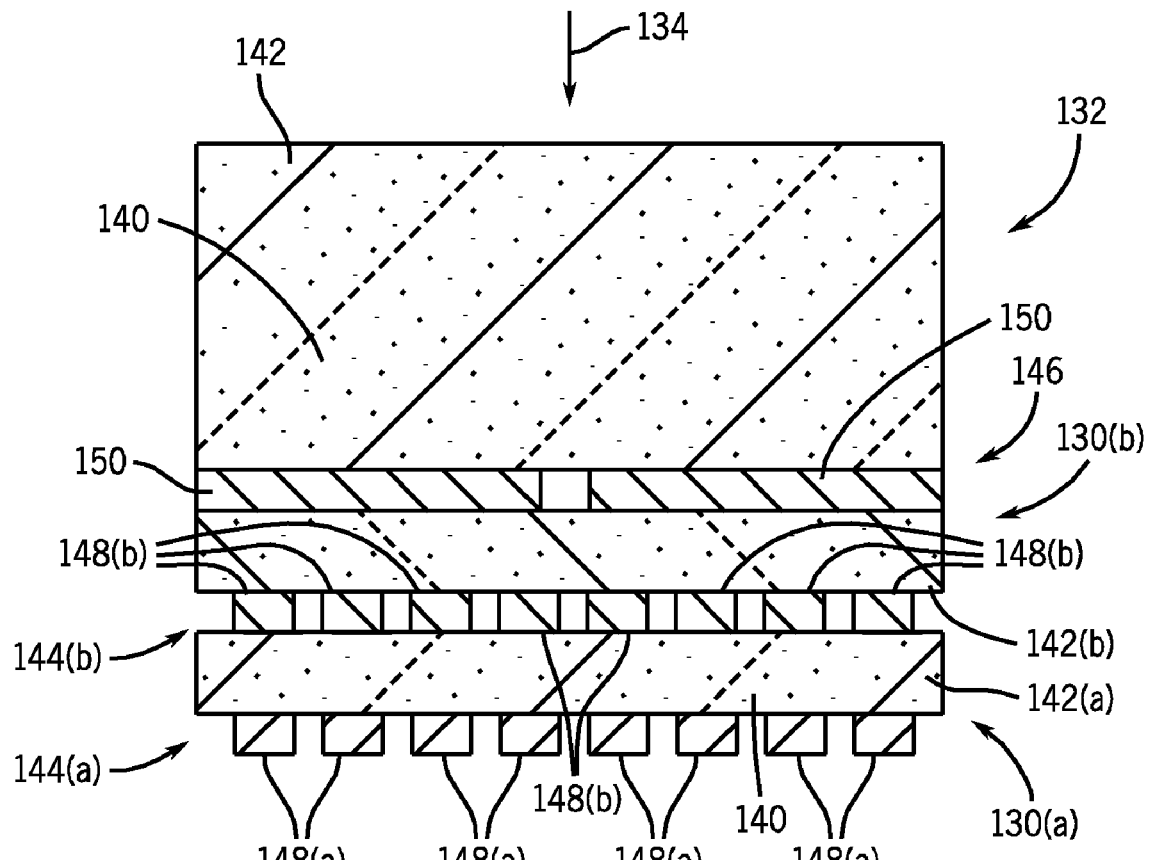
FIG. 15 is a cross-sectional schematic view similar to FIGS. 13-15 illustrating an alternate embodiment of the present invention.

Referring now to FIG. 15, it is contemplated that a detector 126 may be constructed to have more than two detector layers. For example, detector 126 may be designed to have three separate detector layers 130(*a*), 130(*b*), and 132. For purposes of illustration, the detector of FIG. 15 is oriented similar to that shown in FIG. 14 with the addition of another detector layer. As such, the detector illustrated in FIG. 15 includes a relatively thick conversion layer 140 and two relatively thinner conversion layers 142(*a*), 142(*b*). Moreover, the detector element pitch for detector layer 132 is 4× that of detector layers 130(*a*) and 130(*b*). It is contemplated that a detector with the configuration illustrated in FIG. 15 will operate differently than the detectors heretofore described.

Specifically, for the detector 126 of FIG. 15, at lower x-ray flux levels, none of the detector layers will saturate and the data from the smaller detector elements 148(a) and 148(b) will be combined to provide a single signal. That is, assuming that the detector elements 148(a) and 148(b) are one-fourth the pitch of detector elements 150, the count data for detector elements 148(a) and 148(b) will be binned in a 4×4 manner so as to be equivalent to the pitch of detector elements 150 of detector layer 132. For intermediate flux levels, detector layer 132 will saturate and count data from detector layers 130(a) and 130(b) will only be used. The third layer may be constructed to have a saturation threshold of 1000× compared to a 5.0 mm thick, single layer detector assembly having a 1.0 mm detector element pitch.

Figure 16:
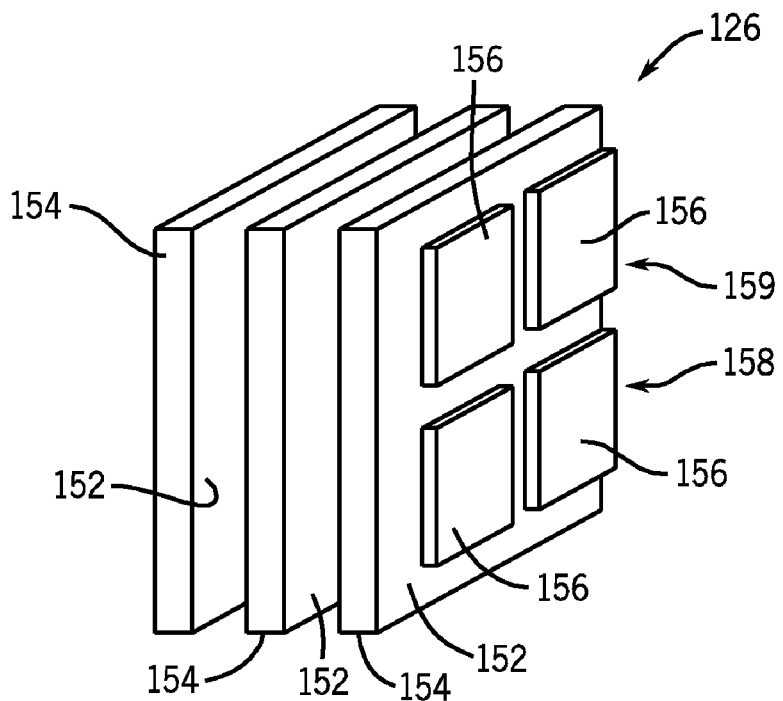
FIG. 16 is a perspective view of a portion of a CT detector with its components oriented in a vertical arrangement.

Referring now to FIG. 16, it is contemplated that a vertical arrangement of the components of a CT detector may be used to also achieve improvements in count rate performance. Detector 126 includes three direct conversion layers that are uniform in their thickness and size. The direct conversion layers 152 are separated from one another by a flex layer 154 and an array of detector elements 156. With this construction the thickness of the conversion layers sets detector element pitch in one direction and the spacing between detector elements defines the pitch in the other direction. Moreover, with this arrangement, response of the detector elements is a function of detector element "height" on a particular conversion layer. For example, a detector element in row 158 of elements having a size of 0.7 mm collects charge from approximately 1% of the x-rays impinged on the detector whereas detector element in row 159 of size 4.3 mm absorbs approximately 99% of the x-rays impinges on the detector. The flux rate saturation for row 158 of elements is therefore 100× greater than for a single 5.0 mm thick detector with 1.0 mm detector element pitch.

As referenced above, the present invention is directed to achieving improvement in saturation characteristics of a CT detector and assembly using multiple direct conversion layers. The present invention is also directed to achieving improvement in saturation characteristics of the CT detector through reduction of detector element size. Each detector element of a CT detector is commonly referred to as a "pixel" and, as such, in one embodiment, the present invention is directed to the "sub-pixelation" of a pixel area.

Figure 17:
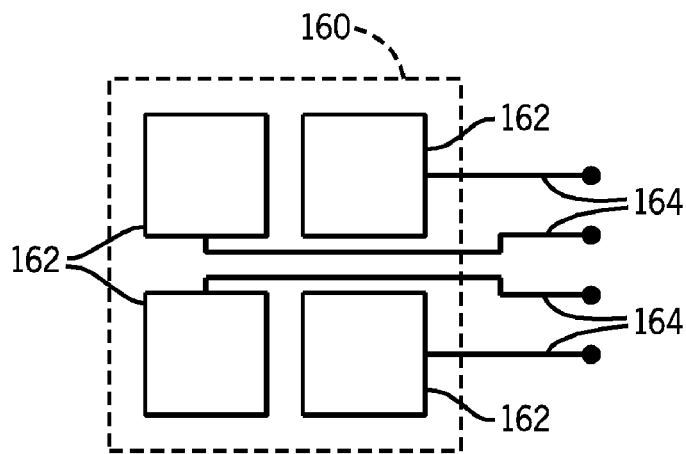
FIG. 17 is a top view schematic illustrating sub-pixelization of a detector element area according to the present invention.

Referring now to FIG. 17, a single pixel area 160 (shown in phantom) is pixelated into four equally sized sub-pixels 162. In the illustrated example, each sub-pixel 162 is connected to a dedicated readout lead 164. Because flux at a pixel is proportional to its area, the combined flux rate saturation threshold of the four separate sub-pixels 162 is 4× that which would be achieved by a single pixel 160 covering the area of the four sub-pixels 162. In addition, each sub-pixel 162 will have a faster charge collection time because of its reduction in size relative to the layer thickness. Faster charge collection time is indicative of a larger saturation flux rate limit over and above the improvement in count rate performance achieved simply by a reduction in detector element size. It is noted that since each sub-pixel 162 is similarly sized, the sub-pixels will saturate at roughly the same x-ray flux level.

Figure 18:
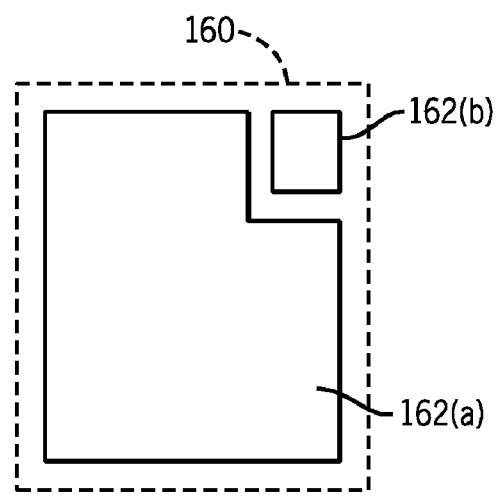
FIG. 18 is a top view of a single CT detector element area illustrating asymmetrical sub-pixelization thereof in accordance with another embodiment of the present invention.

On the other hand and referring to FIG. 18, the area achieved by a single pixel 160 may be pixelated into sub-pixels that have different flux rate characteristics. For example, as shown in FIG. 18, sub-pixel 162(a) is significantly larger than sub-pixel 162(b). This asymmetry in sub-pixel size yields a composite pixel area with different saturation thresholds within the composite pixel area. Specifically, assuming that sub-pixel 162(a) is 20× larger than sub-pixel 162(b), then sub-pixel 162(a) will saturate at an x-ray flux threshold 20× that of sub-pixel 162(b).

Figure 19:
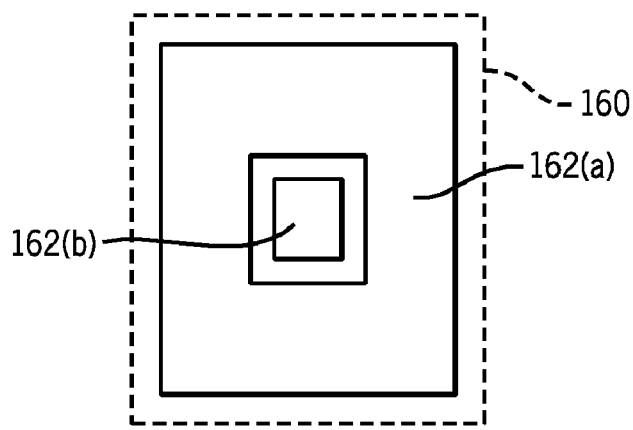
FIG. 19 is a top view of an alternate asymmetrical sub-pixelization for a single CT detector element area in accordance with an alternate embodiment of the present invention.

It is contemplated that any number of orientations may be implemented to orientate sub-pixel 162(a) relative to sub-pixel 162(b). In the arrangement illustrated in FIG. 19, it is believed that the center placement of sub-pixel 162(b) improves cross-talk characteristics between the sub-pixels. That is, in the illustrated arrangement, sub-pixel 162(b) is less likely to be affected by neighboring sub-pixels and, as such, may be more immune from cross-talk from sub-pixel 162(a) when compared to the arrangement of FIG. 18.

It is recognized that flux rate is not uniform across a CT detector. In this regard, the present invention also includes an x-ray flux management system that detects and/or anticipates saturation of a given portion of a CT detector such that appropriate corrective measures may be taken. For example, it is well-known that the extremities of a CT detector assembly often will receive more x-ray flux than the center portions of the CT detector assembly due to subject and pre-subject filter attenuation profiles. As such, it is contemplated that post-acquisition logic may be used to only use the output of non-saturated channels for image reconstruction. In another embodiment, saturation of given portions of the CT detector assembly is anticipated and, as a result, a binning scheme is established such that those portions of the CT detector expected not to saturate are electrically connected to the scanner's DAS and those portions expected to saturate are not. In yet another embodiment, connectivity of the detector elements to the system DAS is determined on a per view basis during data acquisition. That is, previous view data and other priori information is used to connect the detector elements to the DAS. This scheme provides a dynamic, yet flexible binning of the detector elements during data acquisition. In another embodiment, connectivity of the detector elements to the DAS is controlled in real-time. In this regard, connectivity can be changed during the acquisition of data for a given view such that connections are opened if high photon rate is detected.

Figure 20:
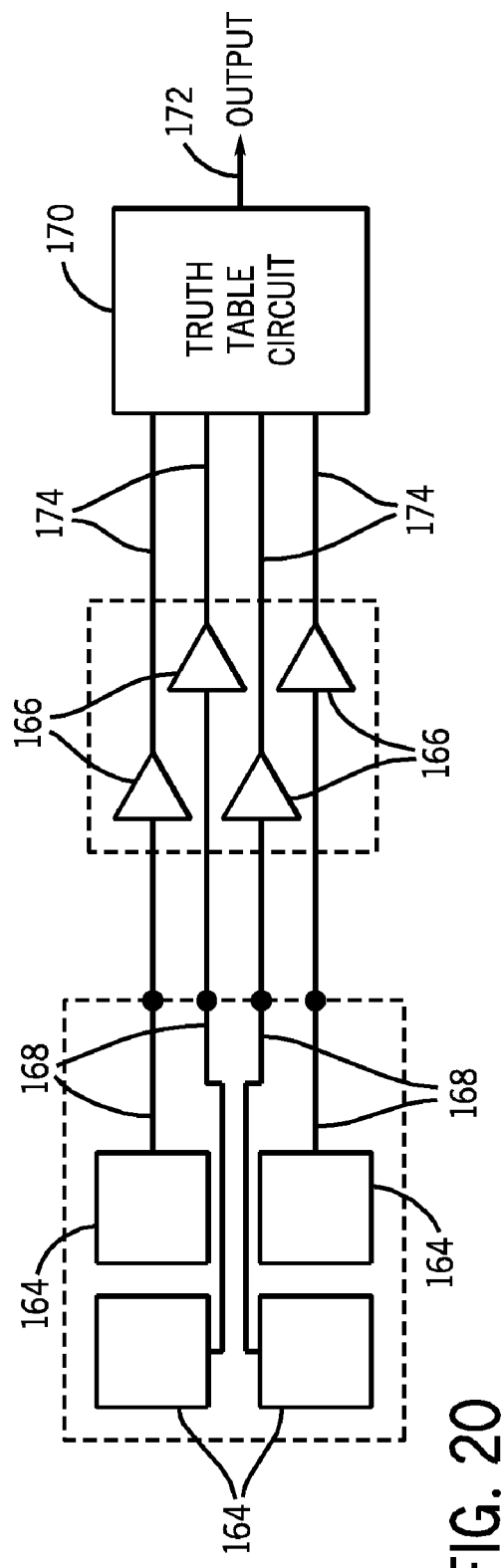
FIG. 20 is a block schematic illustrating combining the output of each sub-pixel of a given CT detector element area in accordance with another embodiment of the present invention.

Shown in FIG. 20 is a schematic of a group of detector elements or sub-pixels 164 for a given layer or array of detector elements with each sub-pixel 164 electrically routed to a respective data system input 166. In the illustrated example, the group is comprised of four sub-pixels 164 and, as such, four outputs 168 are provided to four data system inputs 166. The four outputs of the 4×4 DAS channels 166 are input to a truth table circuit 170. The output 172 of the truth table circuit 170 is a linear combination of the four inputs 174 to the truth table circuit 170 depending on whether any of the inputs are saturated. Although each of the sub-pixels illustrated in FIG. 20 is designed to saturate at the same x-ray flux, it is possible given the contour of the subject being imaged and pre-subject filtering for one sub-pixel of the group to saturate without saturation of a neighboring sub-pixel.

The table below sets out a truth table for combining the outputs of the four sub-pixels. In the truth table, a value of "1" is indicative of non-saturation whereas a value of "0" is. As such, if none of the sub-pixels is saturated, a value of "1" will be input to the truth table circuit 170 for each of the sub-pixels. The truth table indicates that in such a circumstance the outputs from all the sub-pixels are considered acceptable and combined to provide a single output for that group of sub-pixels. On the other hand, if channel "A" or, more precisely, the sub-pixel associated with channel "A", saturates, but the other sub-pixels have not, then the sum of the non-saturated channels is output by the truth table circuit and the data associated with the saturated channel is ignored. For instance, assuming a pixel area composed of one sub-pixel that has a higher x-ray flux saturation threshold higher than another sub-pixel within the pixel area, when x-ray flux is low, both sub-pixels provide a valid output that is summed by the truth table circuit to provide a single output comprised of the count data from both sub-pixels. When the x-ray flux reaches a level to saturate only one of the sub-pixels, data from the non-saturated sub-pixel is the only data output by the truth table circuit.

TABLE 1

LOGIC MAP

| A | B | C | D | Output |
|---|---|---|---|---|
| 1 | 1 | 1 | 1 | A + B + C + D |
| 1 | 1 | 1 | 0 | A + B + C |
| 1 | 1 | 0 | 1 | A + B + D |
| 1 | 1 | 0 | 0 | A + B |
| 1 | 0 | 1 | 1 | A + C + D |
| 1 | 0 | 1 | 0 | A + C |
| 1 | 0 | 0 | 1 | A + D |
| 1 | 0 | 0 | 0 | A |
| 0 | 1 | 1 | 1 | B + C + D |
| 0 | 1 | 1 | 0 | B + C |
| 0 | 1 | 0 | 1 | B + D |
| 0 | 1 | 0 | 0 | B |
| 0 | 0 | 1 | 1 | C + D |
| 0 | 0 | 1 | 0 | C |
| 0 | 0 | 0 | 1 | D |
| 0 | 0 | 0 | 0 | Flag |

It is recognized that a number of techniques may be used to determine saturation of a given sub-pixel. For example, the count rate data for a given sub-pixel may be compared to a threshold and if the count rate determined by the sub-pixel exceeds the threshold, a saturation value of "0" will be input to the truth table circuit for that sub-pixel. For instance, if the detector system is designed to count photons using direct conversion detectors with a one million count per second saturation threshold, then this threshold would be the threshold level imposed on each sub-pixel, or some percentage thereof to provide a margin less than the saturation threshold.

It is also contemplated that a flexible binning of sub-pixels within a given pixel area, such as that described above, may be achieved to further enhance the ability of the detector to output photon count data despite saturation of some portions of the detector. That described with respect to FIG. 20 was a signal management scheme that utilized a single DAS channel for each sub-pixel. However, given the number of sub-pixels within a single CT detector, a single DAS channel per sub-pixel may not be feasible. Accordingly, the present invention also contemplates a signal control scheme that utilizes one DAS channel for a group of sub-pixels. In this regard, the number of DAS channels needed may be equivalent to that needed for a CT detector not incorporating sub-pixelation.

Figure 21:
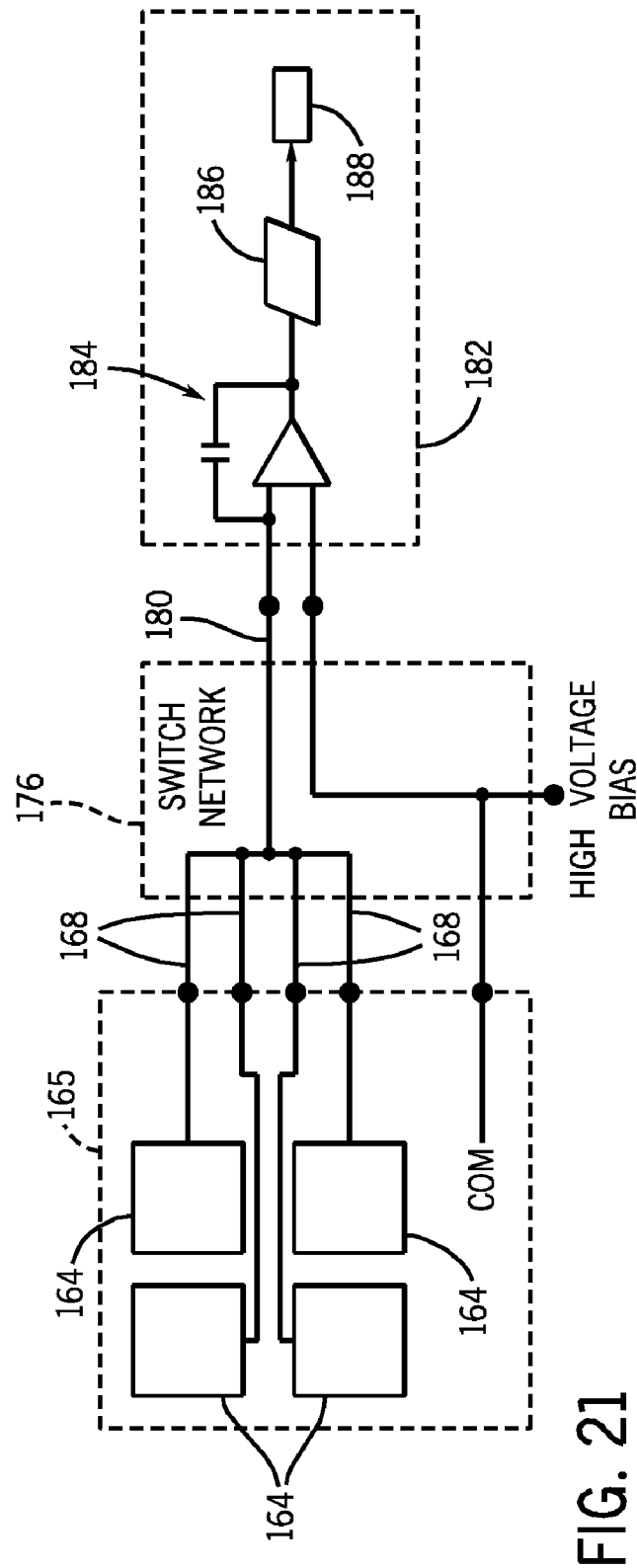
FIG. 21 is a circuit schematic illustrating a flexible binning of sub-pixel outputs of a given CT detector element area in accordance with another embodiment of the present invention.

Referring now to FIG. 21, a switch network-based signal management system is shown whereupon more than one sub-pixel is dynamically controlled to be connected to a DAS input channel. In this regard, the output of each sub-pixel 164 of a given group of sub-pixels is input to a switch network 176. The switch network is designed to reconnect the outputs of the sub-pixels based on a saturation state of the sub-pixels. The switch network may utilize a truth table to dynamically control connectivity of the sub-pixel output. For those sub-pixels that have saturated, the switch network will discard them such that only non-saturated data is included in output 180.

For example, at low x-ray flux, none of the sub-pixels will saturate and, as such, the output 168 from all the sub-pixels 164 will be combined into a single output 180 that is input to DAS 182. DAS 182 includes a signal shaper 184 constructed to extract single photon events from the output of the switch network. It is recognized that a low-noise/high speed charge amplifier (not shown) may be connected to receive the output of the switch network. The output of the amplifier is then input to signal shaper 184. Signal shaper 184 provides an input to an energy level discriminator 186. Energy level discriminator 186 is connected to signal shaper 184 and is designed to filter photons based on their energy level relative to one or more thresholds. To this end, those photons having energy levels outside a desired range are excluded from counting and processing for image reconstruction. Minimally, discriminator 186 is designed to exclude those photons having an energy level corresponding to noise in the system. It is contemplated that multiple thresholds may be used to define energy level ranges. Counting register 188 receives those photons not filtered out by energy level discriminator 186 and is constructed to count the number of photons received at the detector and provide a corresponding output.

DAS 182 counts the number of photons for the given pixel area 165 comprised of the given sub-pixels 164. Since the switch network will not connect the output of a given sub-pixel if it has saturated, DAS will determine a photon count only from the non-saturated sub-pixels. While only four sub-pixels are shown, it is contemplated that a given pixel area may be sub-pixelated into less or more than four sub-pixels.

Figure 22:
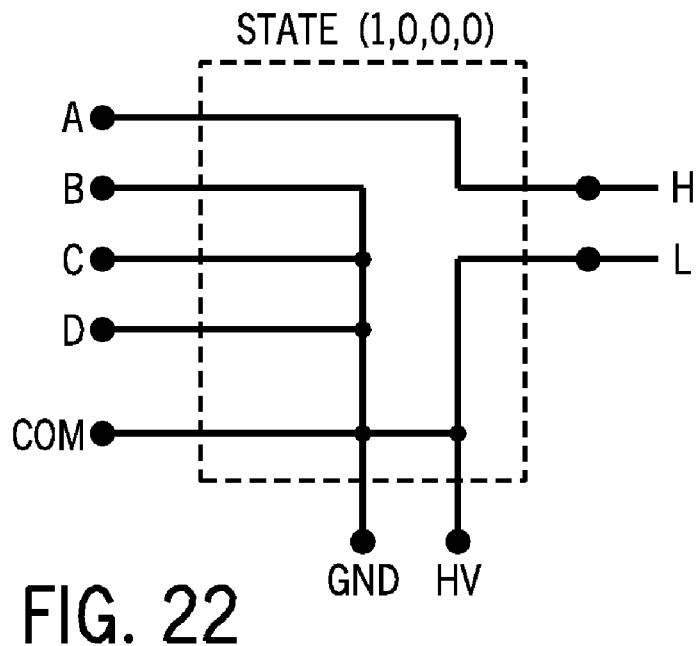
FIGS. 22-23 are circuit schematics illustrating binning of sub-pixel outputs of a given CT detector element area based on the saturation state of each sub-pixel according to a further embodiment of the invention.
Figure 23:
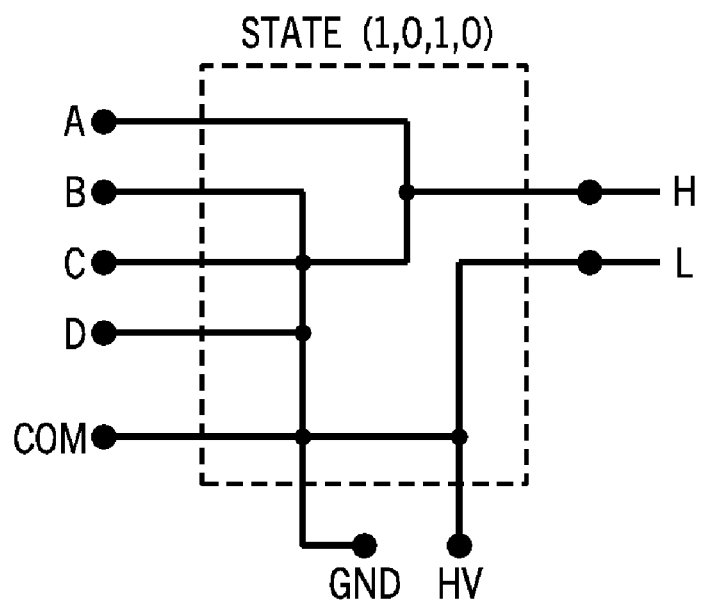

Two switch states are illustrated in FIGS. 22 and 23. As show in FIG. 22, if sub-pixel identified with input "A" is not saturated and all other sub-pixels have saturated, then the output of sub-pixel "A" will only be used for photon counting. As shown in FIG. 23, the switch network may combine any combination of sub-pixel outputs, such as sub-pixels "A" and "C" if those are the only non-saturated sub-pixels.

In an embodiment of the present invention, a first detector is configured to operate in photon counting mode. A second detector is configured to receive x-rays that pass through the first detector and directly convert radiographic energy to electrical signals containing energy discriminatory or photon count data and may be configured to operate in photon counting mode or energy integrating mode. The present invention contemplates a number of configurations for these detectors, their components, and the manner in which data is read out. In a preferred embodiment, the energy discriminatory semiconductors of the first detector are fabricated from Cadmium Zinc Telluride (CZT). One skilled in the art will readily recognize that other materials capable of the direct conversion of radiographic energy may be used. The second detector may include either a conventional scintillator array on a photodiode array or an energy discriminatory semiconductor preferably configured to operate in energy integrating mode.

Figure 24:
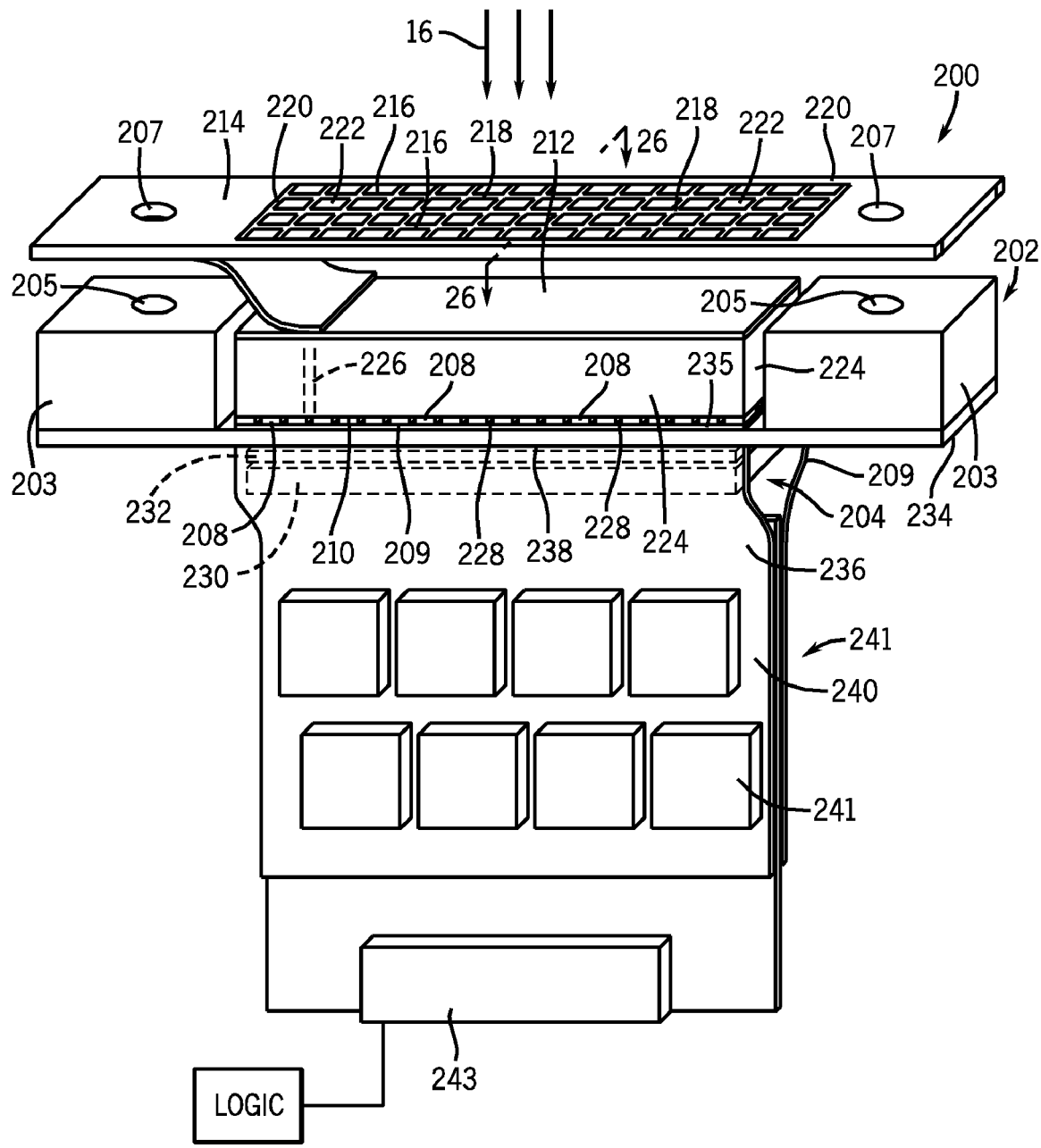
FIG. 24 is a perspective view of a dual-layer detector module according to an embodiment of the present invention.

FIG. 24 illustrates a perspective view of a detector module according to an embodiment of the present invention. A detector module 200 includes a first detector layer 202 that includes a direct conversion material 206 typically made of a semiconductor material such as Cadmium Zinc Telluride (CZT), Cadmium Telluride (CdTe), and the like. First detector layer 202 also has a plurality of pixelated anode contacts 208 attached to a first surface 210 of the direct conversion material 206. Pixelated anode contacts 208 are attached and electrically coupled to a first flexible interconnect 209. Direct conversion material 206 includes a high voltage electrode 212 attached to a second surface 213 of the direct conversion material 206. High voltage electrode 212 effectively operates as a cathode. One skilled in the art will appreciate that high voltage electrode 212 should be relatively thin so as to reduce the x-ray absorption characteristics. Accordingly, high voltage electrode 212 is preferably a few hundred angstroms thick. The high voltage electrode 212 may be affixed to direct conversion material 206 through a metallization process such as vapor deposition and typically includes a metal such as gold, platinum, silver, copper, aluminum, or the like. A high voltage lead 215 is attached to high voltage electrode 212. First detector layer 202 includes spacers 203 positioned on substrate 234 having holes 205 formed therein to serve to align the grid.

A second detector layer 204 of detector module 200 includes a scintillator 230 optically coupled to photodiode array 232. Photodiode array 232 includes a two-dimensional array of diodes, similar to the plurality of diodes 59 illustrated in FIG. 4. Photodiode array 232 is attached and electrically coupled to a second flexible interconnect 236.

A substrate 234 provides a mounting structure and mechanical support for first and second flexible interconnects 209, 236. In the embodiment shown in FIG. 24, substrate 234 is preferably an electrically inactive substrate that does not need to bridge electrical connections thereacross or therethrough. However, one skilled in the art will appreciate that substrate 234 may be electrically active to bridge electrical connections from one portion to another. Substrate 234 also provides a mounting structure and mechanical support for a pair of spacers 203 to which an x-ray attenuating grid assembly 214 may be attached. Grid assembly 214 is positioned to block or attenuate x-rays 16 emitting toward the outer edges, or periphery 224, of direct conversion material 206 as well as to block or attenuate x-rays 16 emitting toward charge-sharing regions 226 of direct conversion material 206.

In a preferred embodiment, a grid assembly is positioned between the first detector and an x-ray source to attenuate x-rays directed toward gaps, or charge-sharing regions, between anodes that form the direct conversion detector. It is generally well known that an x-ray impinging on a direct conversion material will generate a charge in the bulk of the direct conversion material that migrates through the direct conversion material to an anode structure that is positioned to collect the charge. Operation of the detector in an imaging application requires measurement of the charge by collecting the charge on segmented anodes. The segmented anodes define the response area of the detection plane. When an x-ray impinges the direct conversion material in a region near the gaps between the anodes, the charge may be shared between at least two neighboring anodes. Such charge sharing can result in image artifacts or other image problems, which may be mitigated by use of a grid structure that prevents x-rays from impinging the direct conversion material in the charge sharing region.

Detector module 200 includes an x-ray attenuating grid assembly 214. Grid assembly 214 includes a plurality of bars or rungs 216, 218 interspersed between or along a perimeter frame 220 and forming openings 222. Perimeter frame 220 is positioned substantially along perimeter 224 of direct conversion material 206. X-ray attenuating grid assembly 214 includes holes 207 that substantially match with the positions of holes 205 in spacers 203. Holes 207, 205, accordingly, serve as locating features for detector module 200 with respect to an imaging system, such as imaging system 10 of FIG. 1. Perimeter frame 220 is positioned to block or attenuate x-rays emitting from an x-ray source, such as x-ray source 14 of FIG. 1, that are directed toward the outer edges or perimeter 224 of direct conversion material 206. Likewise, rungs 216, 218 are positioned to block or attenuate x-rays that emit from the x-ray source, such as x-ray source 14 of FIG. 1, toward charge-sharing regions 226 of direct conversion material 206.

Still referring to FIG. 24, second detector layer 204 of detector module 200 includes a scintillator 230 optically coupled to photodiode array 232 according to an embodiment of the present invention. The photodiode array 232 is attached and electrically coupled to a second flexible circuit 236, which is mounted to substrate 234.

In operation, x-rays 16 emitting from an x-ray source, such as x-ray source 14 of FIGS. 1 and 2, are directed toward detector module 200. Generally low energy x-rays 16 interact with direct conversion material 206, thus generating an electrical charge therein that migrates to at least one of the pixelated anode contacts 208. The pixelated anode contacts 208, which define the response area of the detection plane, collect the charge that migrates through direct conversion material 206 which may be read out through the first flexible circuit 209 in a DAS 240 having DAS integrated circuits (ICs) 241, wherein the charge is converted to a digital signal. Generally high energy x-rays 16 pass through the first detector layer 202, through substrate 234, through photodiode array 232, and into the scintillator 230 of the second detector layer 204. Photons generated therein travel through the scintillator 230 and impinge upon photodiode array 232. Signals generated within photodiode array 232 may be read out through the second flexible circuit 236 to DAS 240 and DAS ICs 241, wherein the charge is converted to a digital signal and transmitted to, for instance a logic circuit through a connector 243.

During low flux operation, x-rays 16 impinge on direct conversion material 206 of first detector layer 202. First detector layer 202 will generally not saturate during low flux operation, and, for low count rates obtained therein, the first detector layer 202 may be used typically in photon counting mode to form an image. At higher flux rates and with the first detector layer 202 operating typically in photon counting mode and with the second detector layer 204 operating in energy integrating mode, a combination of x-rays detected in both layers is used to form an image for higher count rates obtained in first detector layer 202. At very high flux rates, typically on the order of 5-100 Mcps, the first detector layer 202 saturates, and only the x-rays 16 detected on the second detector layer 204 are used to form an image, typically operating in energy integrating mode.

Figure 25:
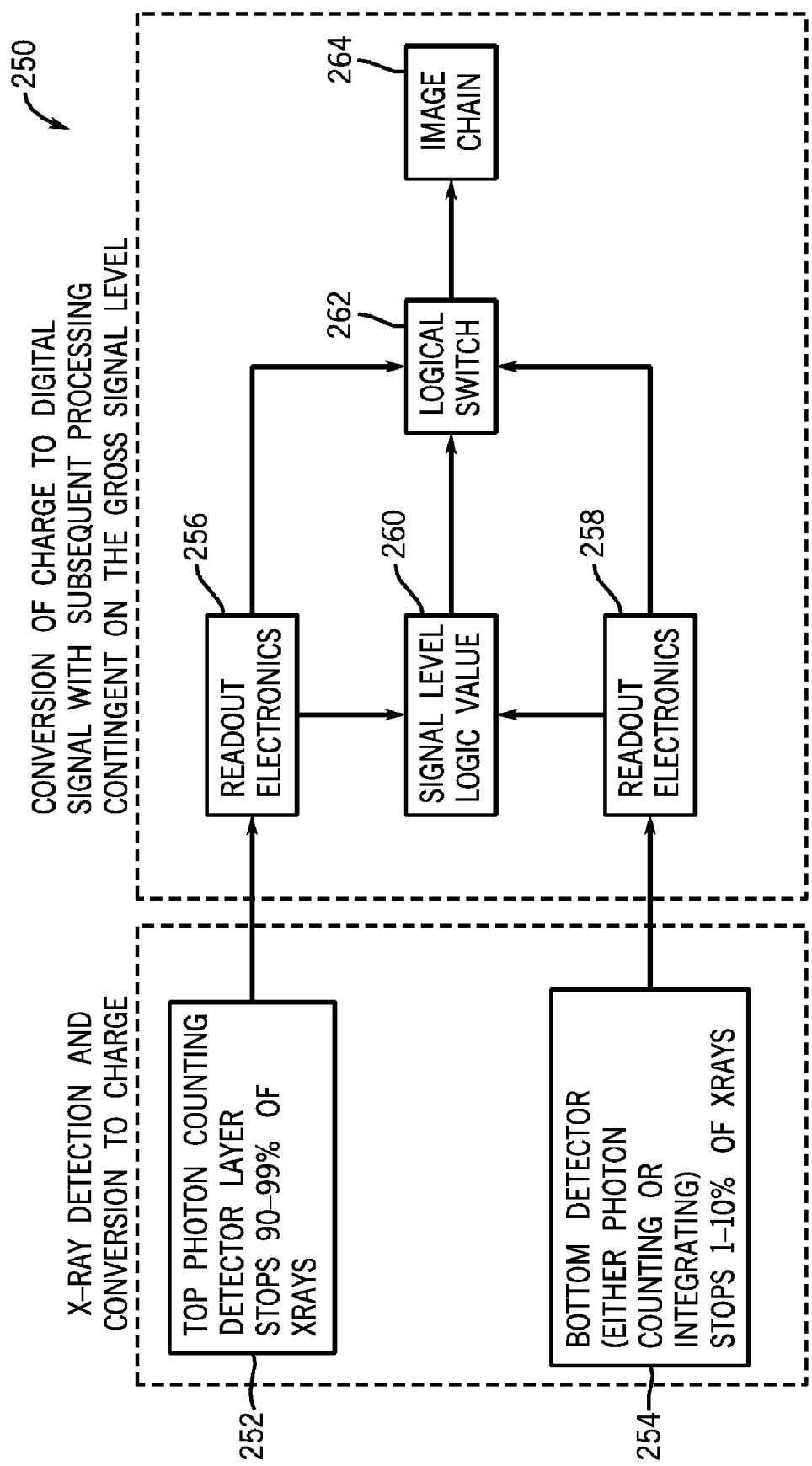
FIG. 25 is a schematic block diagram of a data acquisition pipeline according to an embodiment of the present invention.

FIG. 25 illustrates a flow diagram of a data acquisition pipeline 250 according to an embodiment of the present invention. A pair of detector layers 252, 254 convert detected x-rays to charges. Readout electronics 256 read charges from first detector layer 252, and readout electronics 258 read charges from second detector layer 254. A logic controller 262 receives a gross signal level logic value 260 derived from readout electronics 258, 260. Logic switch/controller 262 compares the gross signal level logic value 260 against threshold values to determine whether to transfer data from only readout electronics 256, only readout electronics 258, or both, to image chain 264 for image reconstruction. It is contemplated that the logic switch/controller 262 may be constructed of discrete electronic components and may include implementation with FPGA, DSP, or ASIC circuits. It is also contemplated that the functions of the logic controller 262 may be performed by a computer processor software, firmware, or other hardware as is commonly understood in the art. Logic controller 262 transfers data from only readout electronics 256, only readout electronics 258, or both to image chain 264 based on the comparison of the gross signal level logic value 260 against the threshold values. The threshold values are set relative to the flux rate at which the first detector layer 252 will saturate. Most generally the logic signal may derive from both layers 252, 254, but one skilled in the art will recognize that the logic signal may be derived from only the first detector layer 252 or the second detector layer 254.

For low flux conditions and when low detection levels occur in readout electronics 258, first detector layer 252 typically does not saturate, and an image can be formed fully and solely from energy discriminating information derived through readout electronics 256. In this case, logic controller 262 preferably transfers information derived from only the first detector layer 252 to image chain 264. For higher flux conditions and when higher detection levels occur in readout electronics 258, some saturation may occur in first detector layer 252, and an image may be formed using information from both the energy discriminating first detector layer 252 and the second detector layer 254 operating in energy integrating mode. In this case, logic controller 262 preferably transfers information derived from both the first detector layer 252 and the second detector layer 254 to image chain 264. For highest flux conditions and when very high detection levels occur in readout electronics 258, first detector layer 252 is typically fully saturated, and an image may be formed fully from the second detector layer 254. In this case, logic controller 262 preferably transfers information derived from only the second detector layer 254 to image chain 264.

FIG. 26 illustrates a section view of the detector module of FIG. 24 along line 26-26. In this embodiment and as described above, detector module 200 includes a first detector layer 202 having direct conversion material 206 with pixelated anode contacts 208 mounted thereon. A high voltage electrode 212 is attached to direct conversion material 206, and a grid assembly 214 is attached to high voltage electrode 212. Pixelated anode contacts 208 are attached and electrically coupled to first flexible circuit 209, which may be mounted to substrate 234. A second detector layer 204 includes a scintillator 230 attached to photodiode array 232, which is attached and electrically coupled to second flexible circuit 236. Second flexible circuit 236 may also be mounted to substrate 234. DAS 240 includes ICs 241 to readout respective first and second detector layers 202, 204.

Figure 28:
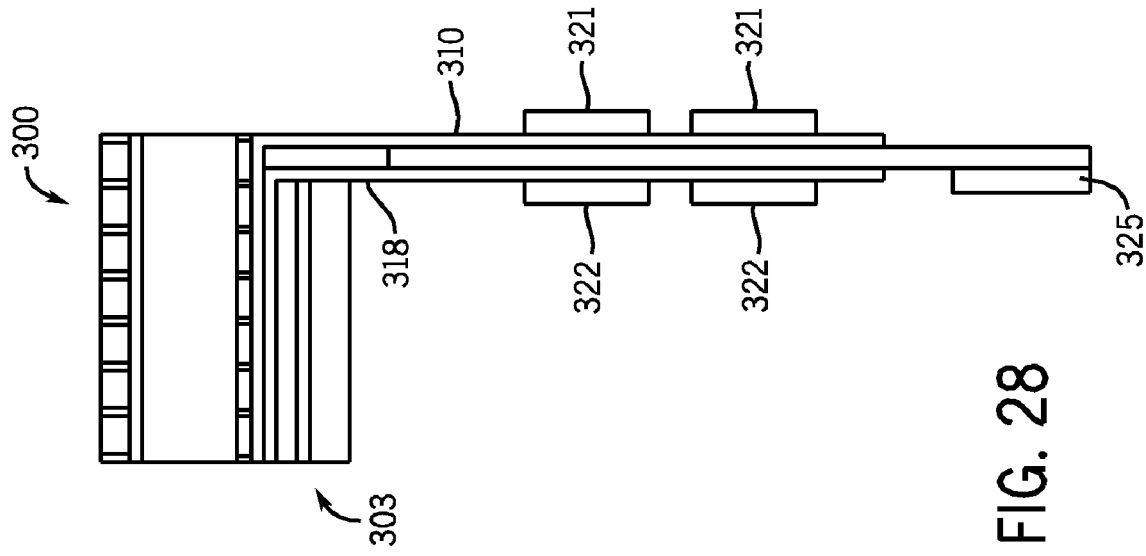

FIGS. 27 and 28 illustrate an alternate detector module embodiment according to the present invention. Detector module 300 includes a first detector layer 301 having direct conversion material 302 with pixelated anode contacts 304 mounted thereon. A high voltage electrode 306 is attached to direct conversion material 302, and a grid assembly 308 is attached to high voltage electrode 306. Pixelated anode contacts 304 are electrically coupled to a first flexible circuit 310 and to ICs 321 of DAS 320. Detector module 300 also includes a second detector layer 303 that has a scintillator 312 attached to a photodiode array 314. In addition to that shown in FIGS. 24 and 26, detector module 300 includes a multi-layer substrate 316 that electrically couples photodiode array 314 to a second flexible circuit 318 and to ICs 322 of DAS 320. Multi-layer substrate 316 contains electrical pathways therethrough to carry electrical signals that derive from the second detector layer 303 into second flexible circuit 318. Electrical signals generated in the first detector layer 301 pass into first flexible circuit 310 and to DAS 320, having ICs 321 mounted thereon, and to connector 325.

As shown in FIG. 27, first and second circuits 310, 318 may extend toward ICs 321, 322 from opposite sides of second detector layer 303. Alternatively, as shown in FIG. 28, first and second circuits 310, 318 may extend toward ICs 321, 322 from the same side of second detector layer 303.

FIG. 29 illustrates an alternate detector module embodiment according to the present invention. Detector module 350 includes a first detector layer 351 having direct conversion material 352 with pixelated anode contacts 354 mounted thereon. A high voltage electrode 356 is attached to direct conversion material 352, and a grid assembly 358 is attached to high voltage electrode 356. Pixelated anode contacts 354 are attached and electrically coupled to a flexible circuit 360 and to ICs 321 of DAS 320. Detector module 350 also includes a second detector layer 353 that has a scintillator 362 attached to a photodiode array 364, which is attached to a multi-layer substrate 366 that electrically couples photodiode array 364 to flexible circuit 360 and to DAS 370. Multi-layer substrate 366 contains electrical pathways therethrough to carry electrical signals which derive from the second detector layer 353 into flexible circuit 360. Electrical signals generated in the first detector layer 351 pass into flexible circuit 360 and to ICs 371 of DAS 370.

Figure 30:
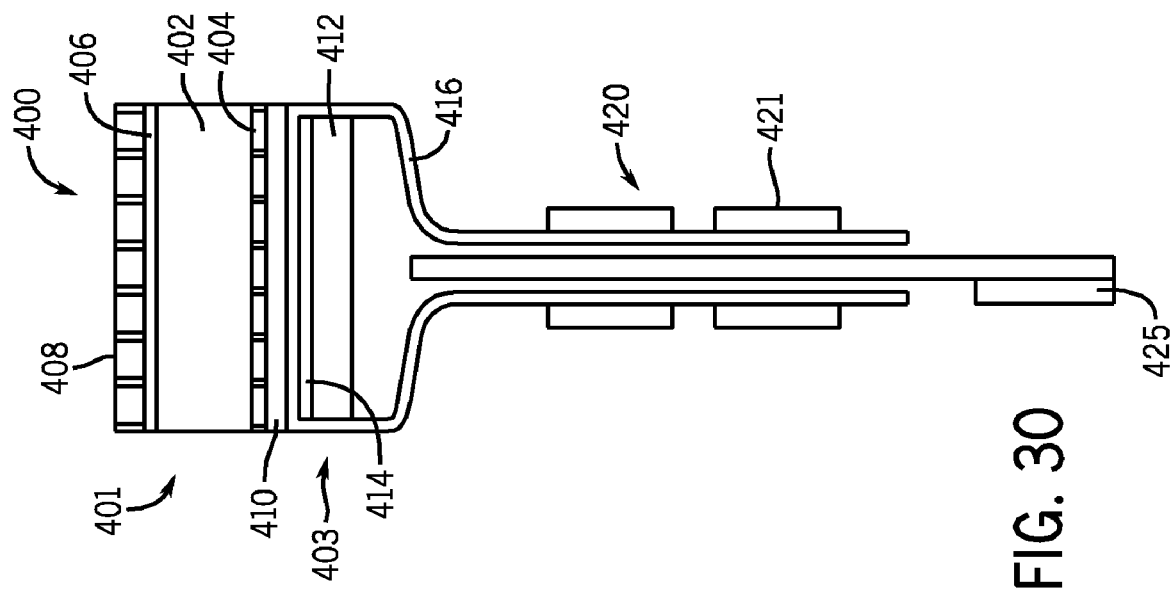

FIG. 30 illustrates an alternate detector module embodiment according to the present invention. Detector module 400 includes a first detector layer 401 having direct conversion material 402 with pixelated anode contacts 404 mounted thereon. A high voltage electrode 406 is attached to direct conversion material 402, and a grid assembly 408 is attached to high voltage electrode 406. Pixelated anode contacts 404 are attached and electrically coupled to a multi-layer substrate 410. Multi-layer substrate 410 contains electrical pathways therethrough to carry electrical signals which derive from the first detector layer 401. Accordingly, electrical signals generated in the first detector layer 401 pass through multi-layer substrate 410, into flexible circuit 416, and to DAS 420. Detector module 400 also includes a second detector layer 403 having a scintillator 412 attached to a photodiode array 414, which is electrically coupled to flexible circuit 416. Electrical signals generated in the second detector layer 403 pass into flexible circuit 416 and to DAS 420, having ICs 421 mounted thereon, to connector 425.

FIG. 31 illustrates an assembly procedure to assemble a detector module according to an embodiment of the present invention. In one embodiment, the assembly procedure corresponds to an assembly of detector module 300 of FIG. 27. In this embodiment, DAS 320 has first flexible circuit 310 and the components 309 of first detector layer 301 mounted thereon. DAS 320 further has second flexible circuit 318 and the components 311 of the second detector layer 303 mounted thereon. Components 309 of the first detector layer 301 include, but are not limited to, direct conversion material 302, pixelated anode contacts 304, high voltage electrode 306, and grid assembly 308. Components 311 of the second detector layer 303 include, but are not limited to, multi-layer substrate 316, photodiode array 314, and scintillator 312. During assembly of detector module 300, ICs 321, 322 of DAS 320 are mounted on flexible circuits 310, 318, which are each mounted to interconnect board 323. Components 309 of first detector layer 301 are attached to first flexible circuit 310, and components 311 of second detector layer 303 are attached to second flexible circuit 318. In one embodiment, second detector layer 303 is folded into position 330, followed by the folding of first detector layer 301 into position 332. First and second flexible circuits 310, 318 are preferably bonded together so that first and second detector layers 301, 303 remain substantially overlapped. One skilled in the art will recognize that other detector assemblies illustrated, as in, for instance, FIGS. 26 and 28-30, may be assembled in a similar fashion.

FIG. 32 illustrates an alternate detector module embodiment according to another embodiment of the present invention. Detector module 500 includes a first detector layer 502 having direct conversion material 503 with pixelated anode contacts 504 mounted thereon. A high voltage electrode 506 is attached to direct conversion material 503, and a grid assembly 508 is attached to high voltage electrode 506. Pixelated anode contacts 504 are attached and electrically coupled to a first flexible circuit 510. Detector module 500 also includes a second detector layer 512 that has a scintillator 514 attached and electrically coupled to a photodiode array 516, which is attached to a multi-layer substrate 518 having electrical pathways therethrough to electrically couple and carry electrical signals which derive from the second detector layer 512 to a second flexible circuit 520. First flexible circuit 510 and second flexible circuit 520 are also electrically coupled together. ICs 522, connected to first flexible circuit 510, are mounted adjacent to scintillator 514 rather than being mounted on interconnect board 525. Electrical signals may be processed by ICs 522 or by ICs 524, thus placing some of the ICs 522 closer to their source of signals. Accordingly, capacitance of the overall circuit may be reduced because of the close proximity of ICs 522 to the second detector layer 512.

Figure 33:
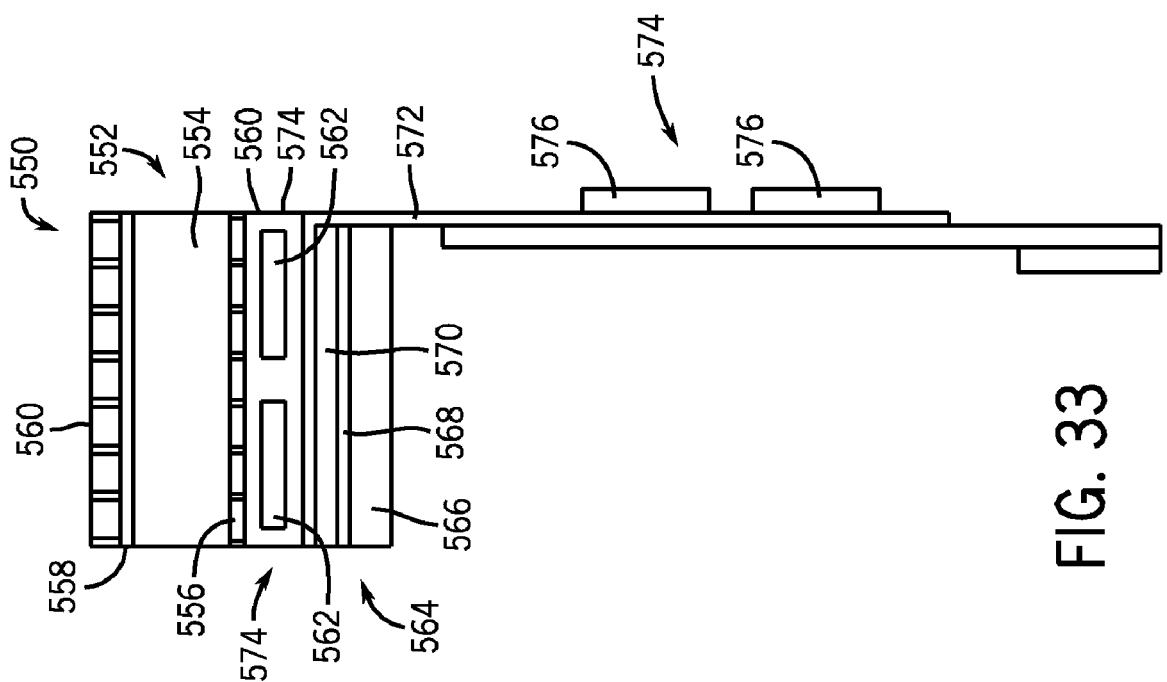

FIG. 33 illustrates an alternate detector module embodiment according to another embodiment of the present invention. Like the embodiment of FIG. 32, some of the ICs 562 are positioned closer to the electrical source, likewise reducing the overall capacitance of the electrical circuit. Detector module 550 includes a first detector layer 552 having direct conversion material 554 with pixelated anode contacts 556 mounted thereon. A high voltage electrode 558 is attached to direct conversion material 554, and a grid assembly 560 is attached to high voltage electrode 558. Pixelated anode contacts 556 are attached and electrically coupled to a chip package 560 having ICs 562 therein. Electrical signals generated in first detector layer 552 pass into chip package 560 which in turn provides signals that are passed into flexible circuit 572. Accordingly, capacitance of the overall circuit may be reduced. Detector module 550 includes a second detector layer 564 having scintillator 566 attached and electrically coupled to photodiode array 568. Photodiode array 568 is attached to multi-layer substrate 570, which is attached to flexible circuit 572. Electrical signals generated in the second detector layer 564 pass through the multi-layer substrate 570, which are passed, likewise, into flexible circuit 572 and carried to ICs 576. DAS 574 includes ICs 562 and ICs 576.

Figure 34:
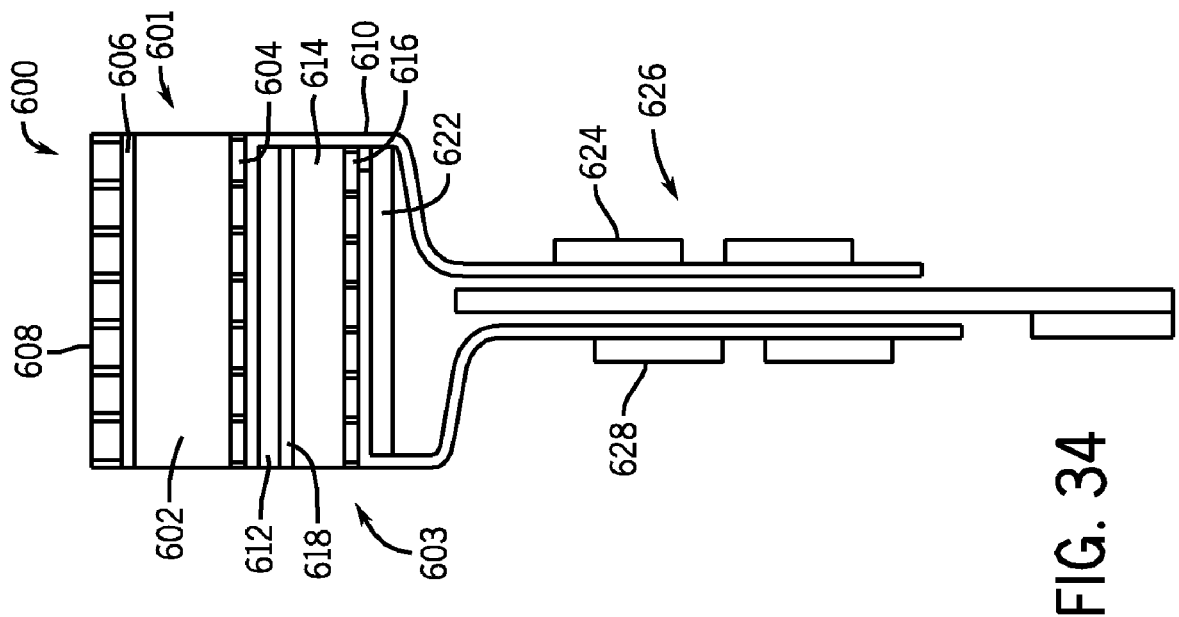
Figure 36:
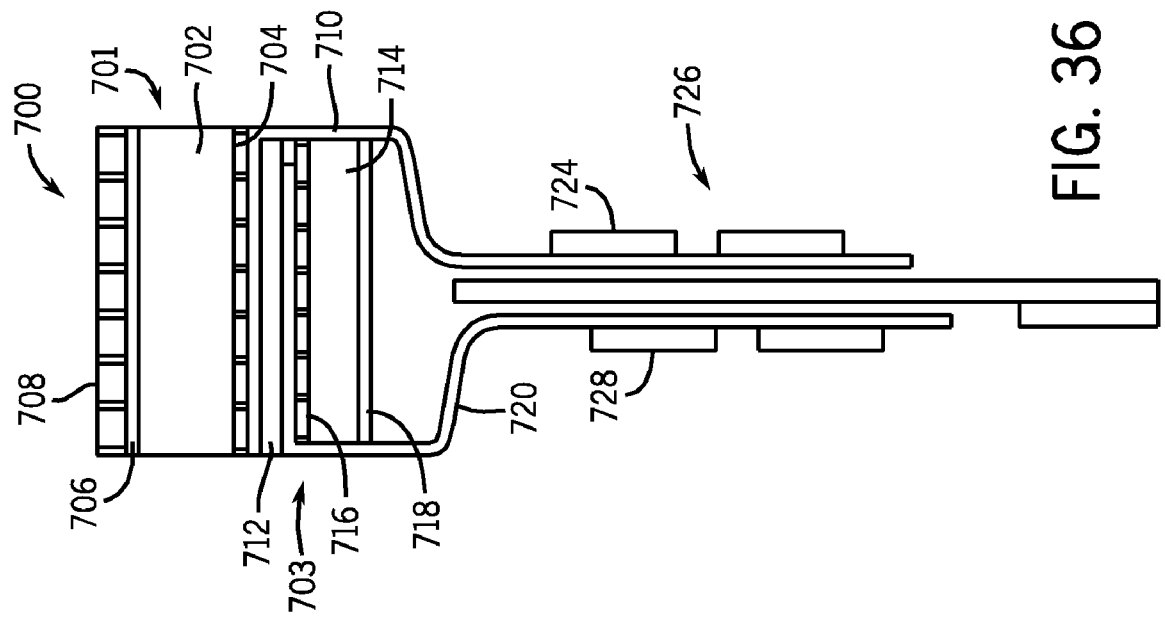
Figure 35:
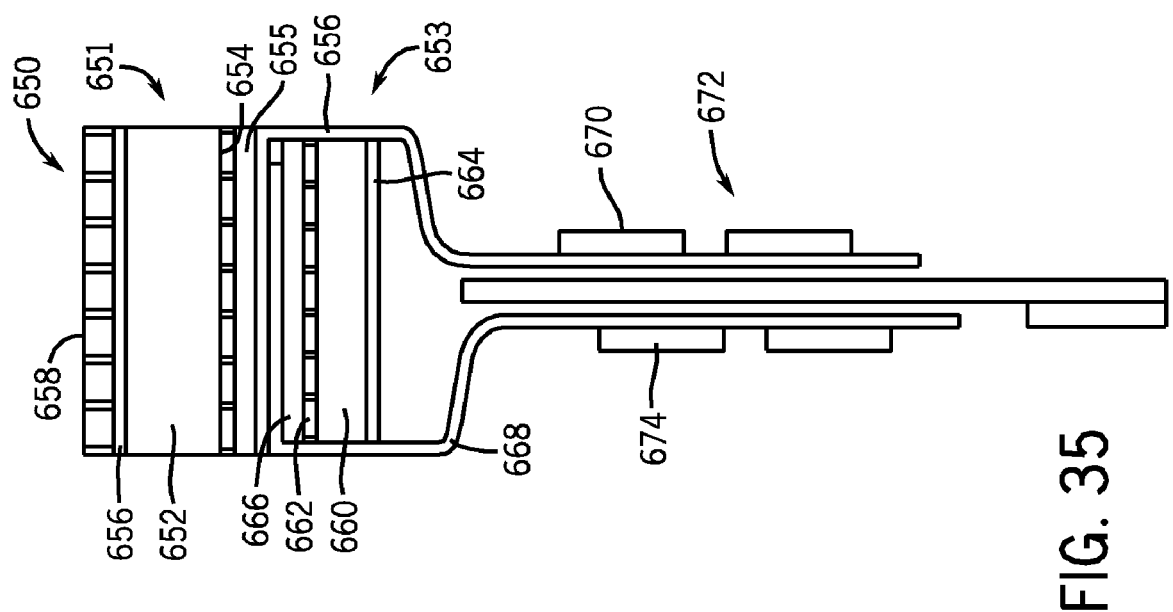

FIGS. 34-36 illustrate alternate detector module embodiments according to the present invention. In these illustrated embodiments, layered detectors include two layers of direct conversion materials. As such, the direct conversion materials may be configured to operate in energy discriminating or energy integrating mode.

FIG. 34 illustrates a detector module according to an embodiment of the present invention. Detector module 600 includes a first detector layer 601 having direct conversion material 602 with pixelated anode contacts 604 mounted thereon. A high voltage electrode 606 is attached to direct conversion material 602, and a grid assembly 608 is attached to high voltage electrode 606. Pixelated anode contacts 604 are attached and electrically coupled to a first flexible circuit 610. First flexible circuit 610 is mounted to substrate 612. Detector module 600 also includes a second detector layer 603 having direct conversion material 614 with pixelated anode contacts 616 mounted thereon. A high voltage electrode 618 is attached to direct conversion material 614. Pixelated anode contacts 616 are attached to a second flexible circuit 620, which is attached to a substrate 622. Electrical signals generated in the first detector layer are carried to ICs 624 of DAS 626, and electrical signals generated in second detector layer 603 are carried out to ICs 628 through second flexible circuit 620.

FIG. 35 illustrates an alternate detector module embodiment according to the present invention. Detector module 650 includes a first detector layer 651 having direct conversion material 652 with pixelated anode contacts 654 mounted thereon. High voltage electrode 656 is attached to direct conversion material 652, and a grid assembly 658 is attached to high voltage electrode 656. Pixelated anode contacts 654 are attached and electrically coupled to a multi-layer substrate 655, which is attached and electrically coupled to a first flexible circuit 656. Detector module 650 also includes a second detector layer 653 having direct conversion material 660 with pixelated anode contacts 662 mounted thereon. High voltage electrode 664 is attached to direct conversion material 660. Pixelated anode contacts 662 are attached and electrically coupled to a multi-layer substrate 666, which in turn is attached and electrically coupled to a second flexible circuit 668. Electrical signals generated in the first detector layer are carried out to ICs 670 of DAS 672, and electrical signals generated in second detector layer 653 are carried out to ICs 674 of DAS 672 through second flexible circuit 668.

FIG. 36 illustrates an alternate detector module embodiment according to the present invention. Detector module 700 includes a first detector layer 701 having direct conversion material 702 with pixelated anode contacts 704 mounted thereon. High voltage electrode 706 is attached to direct conversion material 702, and a grid assembly 708 is attached to high voltage electrode 706. Pixelated anode contacts 704 are attached and electrically coupled to a first flexible circuit 710. First flexible circuit 710 is attached to substrate 712. Detector module 700 also includes a second detector layer 703 having direct conversion material 714 with pixelated anode contacts 716 mounted thereon. High voltage electrode 718 is attached to direct conversion material 714. Pixelated anode contacts 716 are attached to a second flexible circuit 720, which is attached to substrate 712. Electrical signals generated in the first detector layer are carried out to ICs 724 of DAS 726, and electrical signals generated in second detector layer 703 are carried out to ICs 728 through second flexible circuit 720.

Figure 37:
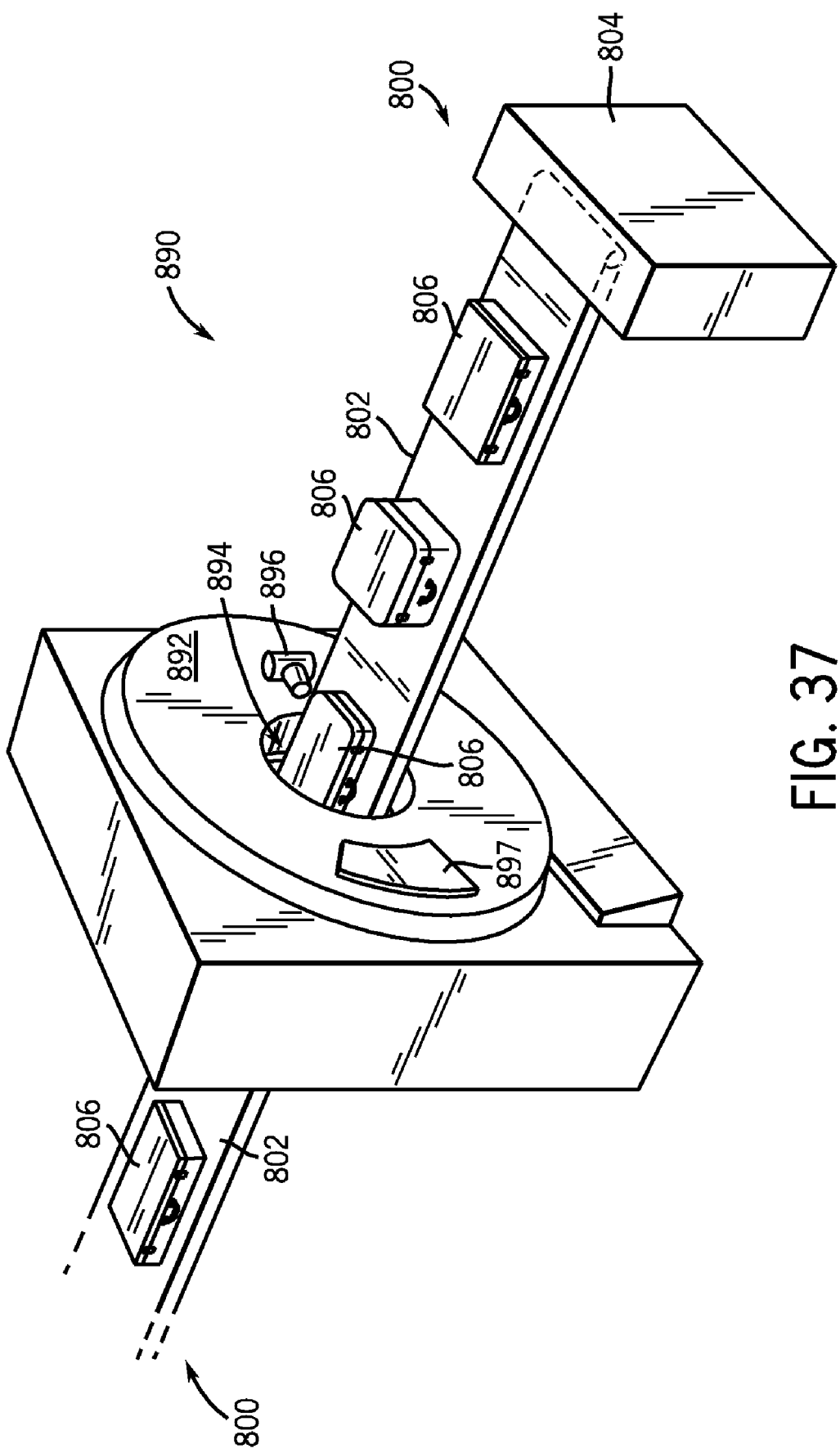
FIG. 37 is a pictorial view of a CT system for use with a non-invasive package inspection system.

Referring now to FIG. 37, package/baggage inspection system 890 incorporating a detector consistent with described herein is shown. System 890 includes a rotatable gantry 892 having an opening 894 therein through which packages or pieces of baggage may pass. The rotatable gantry 892 houses a radiation source 896 as well as a detector assembly 898. A conveyor system 800 is also provided and includes a conveyor belt 802 supported by structure 804 to automatically and continuously pass packages or baggage pieces 806 through opening 894 to be scanned. Objects 806 are fed through opening 894 by conveyor belt 802, imaging data is then acquired, and the conveyor belt 802 removes the packages 806 from opening 894 in a controlled and continuous manner. As a result, postal inspectors, baggage handlers, and other security personnel may non-invasively inspect the contents of packages 806 for explosives, knives, guns, contraband, etc.

Therefore, in accordance with one embodiment of the present invention, a CT detector includes a first detector configured to convert radiographic energy to electrical signals representative of energy sensitive radiographic data and a second detector configured to convert radiographic energy to electrical signals representative of energy sensitive radiographic data and positioned to receive x-rays that pass through the first detector. A logic controller is electrically connected to the first detector and the second detector and is configured to receive a logic output signal from the second detector indicative of an amount of a saturation level of the first detector, compare the logic output signal to a threshold value, and output, based on the comparison, electrical signals from the first detector, the second detector, or a combination thereof to an image chain.

In accordance with another embodiment, a radiographic imaging system includes a radiation source configured to project x-rays toward a subject to be scanned, a detector assembly comprising a first detector layer and a second detector layer, the second layer positioned to receive x-rays from the radiation source that pass through the first detector layer, each of the first and second layers configured to receive x-rays projected from the radiation source and convert radiographic energy to electrical signals representative of energy sensitive radiographic data, and a device configured to receive data indicative of a flux rate in at least one of the first and second detector layers, determine whether to output electrical signals in the first detector layer for image reconstruction based on the received data, and determine whether to output electrical signals in the second detector layer for image reconstruction based on the received data.

According to another embodiment, a method of fabricating an imaging system includes providing an x-ray source, positioning a first detector to receive x-rays that emit from the x-ray source, positioning a second detector to receive x-rays that emit from the x-ray source and that pass through the first detector, and electrically coupling a logic device to the first and second detectors, the logic device configured to indicate a level of x-ray flux in one of the first and second detectors.

The present invention has been described in terms of the preferred embodiment, and it is recognized that equivalents, alternatives, and modifications, aside from those expressly stated, are possible and within the scope of the appending claims.

What is claimed is:

1. A CT detector comprising:
    a first detector configured to convert radiographic energy to electrical signals representative of energy sensitive radiographic data;
    a second detector configured to convert radiographic energy to electrical signals representative of energy sensitive radiographic data and positioned to receive x-rays that pass through the first detector; and
    a logic controller electrically connected to the first detector and the second detector, the logic controller configured to:
        receive a logic output signal from the second detector indicative of an amount of a saturation level of the first detector;
        compare the logic output signal to a threshold value; and
        output, based on the comparison, electrical signals from the first detector, the second detector, or a combination thereof to an image chain.

2. The CT detector of claim 1 wherein the logic controller is one of an FPGA circuit, a DSP circuit, an ASIC circuit, software implemented on a computer readable storage medium, and firmware.

3. The CT detector of claim 1 wherein the first detector comprises an energy discriminating detector having a direct conversion layer.

4. The CT detector of claim 3 further comprising at least one of a charge-sharing region and an edge-trapping region formed in the direct conversion layer and further comprising an x-ray attenuating material positioned to attenuate x-rays directed toward the at least one of a charge-sharing region and an edge-trapping region.

5. The CT detector of claim 3 wherein the energy discriminating detector is configured to operate in photon counting mode.

6. The CT detector of claim 1 wherein the second detector comprises an energy discriminating detector configured to operate in one of a photon counting mode and an energy integrating mode.

7. The CT detector of claim 1 wherein the second detector comprises a scintillating layer optically attached to a photodiode array.

8. The CT detector of claim 1 wherein the logic controller is further configured to output electrical signals converted in only the first detector when the logic output signal indicates that no saturation occurred in the first detector.

9. The CT detector of claim 1 wherein the logic controller is further configured to output electrical signals converted in only the second detector when the logic output signal indicates that the first detector is saturated.

10. The CT detector of claim 1 wherein the logic output signal is indicative of a flux rated incident on the first detector.

11. A radiographic imaging system comprising:
    a radiation source configured to project x-rays toward a subject to be scanned;
    a detector assembly comprising a first detector layer and a second detector layer, the second layer positioned to receive x-rays from the radiation source that pass through the first detector layer, each of the first and second layers configured to receive x-rays projected from the radiation source and convert radiographic energy to electrical signals representative of energy sensitive radiographic data; and
    a controller configured to:
        receive a logic output signal from the second detector layer indicative of a saturation level of the first detector layer;
        compare the logic output signal to a threshold value; and
        output electrical signals from the first detector layer, the second detector layer, or a combination thereof to an image chain for image reconstruction based on the received data.

12. The radiographic imaging system of claim 11 wherein the device is a logic controller comprising one of an FPGA circuit, a DSP circuit, an ASIC circuit, software written on a computer readable storage medium, and firmware.

13. The radiographic imaging system of claim 11 wherein the first detector layer comprises a direct conversion material and an array of electrical contacts connected to the direct conversion material.

14. The radiographic imaging system of claim 13 further comprising at least one of a charge-sharing region and an edge-trapping region formed in the direct conversion material and further comprising an x-ray attenuating material positioned to attenuate x-rays directed toward the at least one of a charge-sharing region and an edge-trapping region.

15. The radiographic imaging system of claim 11 wherein the first detector layer is configured to operate in photon counting mode.

16. The radiographic imaging system of claim 11 wherein the second detector layer is configured to operate in energy integrating mode.

17. The radiographic imaging system of claim 11 wherein the second detector layer comprises a direct conversion material and an array of electrical contacts connected to the direct conversion material.

18. The radiographic imaging system of claim 11 wherein the second detector layer further comprises a scintillator array optically attached to a photodiode array.

19. A method of fabricating an imaging system, the method comprising:
    providing an x-ray source;

positioning a first detector to receive x-rays that emit from the x-ray source;

positioning a second detector to receive x-rays that emit from the x-ray source and that pass through the first detector; and electrically coupling a logic device to the first and second detectors, the logic device configured to:
  receive a logic output signal from the second detector indicative of a saturation level of the first detector;
  compare the logic output signal to a threshold value; and
  output, based on the comparison, electrical signals from the first detector. the second detector, or a combination thereof to an image chain.

20. The method of claim 19 wherein positioning the first detector comprises positioning a direct conversion material to receive x-rays that emit from the x-ray source and electrically coupling a plurality of metallized contacts to the direct conversion material.

21. The method of claim 19 further comprising configuring the first detector layer to operate in photon counting mode.

22. The method of claim 19 further comprising configuring the second detector layer to operate in photon counting mode.

23. The method of claim 19 further comprising configuring the second detector layer to operate in energy integrating mode.

24. The method of claim 19, wherein the imaging system comprises a CT imaging system.

* * * * *